(12) United States Patent
Lehmbeck

(10) Patent No.: US 6,352,841 B1
(45) Date of Patent: Mar. 5, 2002

(54) HOST CELLS AND METHODS OF PRODUCING PROTEINS

(75) Inventor: Jan Lehmbeck, Vekso (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/252,509

(22) Filed: Feb. 18, 1999

Related U.S. Application Data

(63) Continuation of application No. PCT/DK97/00397, filed on Sep. 19, 1997.

(30) Foreign Application Priority Data

Sep. 19, 1996 (DK) .............................................. 1024/96

(51) Int. Cl.$^7$ ................................................. C12P 21/02
(52) U.S. Cl. ................ 435/69.1; 435/254.3; 435/254.7
(58) Field of Search ............................ 435/69.1, 254.3, 435/254.7

(56) References Cited

U.S. PATENT DOCUMENTS

| 5,480,794 | A |   | 1/1996  | Peoples et al. |          |
|-----------|---|---|---------|----------------|----------|
| 5,674,728 | A | * | 10/1997 | Buxton et al.  | 435/225  |

FOREIGN PATENT DOCUMENTS

| EP | 0 327 797    | 8/1989  |
|----|--------------|---------|
| WO | WO 89/04866  | 6/1989  |
| WO | WO 90/00192  | 1/1990  |
| WO | WO 92/17595  | 10/1992 |
| WO | WO 96/04373  | 2/1996  |
| WO | WO 96/05316  | 2/1996  |
| WO | WO 96/29391  | 9/1996  |
| WO | WO 97/35956  | 10/1997 |

OTHER PUBLICATIONS

Jaton–Ogay et al., Molecular Microbiology, vol. 14, No. 5, pp. 917–928 (1994).
Tatsumi et al., Mol Gen Genet, vol. 219, pp. 33–38 (1989).

* cited by examiner

Primary Examiner—James Ketter
(74) Attorney, Agent, or Firm—Elias J. Lambiris

(57) ABSTRACT

The present invention relates to novel host cells and to methods of producing proteins. More specifically the invention relates to a host cell useful for the expression of heterologous proteins, in which the host cell has been genetically modified in order to express significantly reduced levels of a metalloprotease and an alkaline protease. Moreover the invention relates to a method of producing a heterologous protein, which method comprises cultivating the host cell in a suitable growth medium, followed by recovery of the desired protein.

20 Claims, 9 Drawing Sheets

SEQUENCE LISTING

<160> NUMBER OF SEQ ID NOS: 6

<210> SEQ ID NO 1
<211> LENGTH: 2052
<212> TYPE: DNA
<213> ORGANISM: Fusarium oxysporum
<220> FEATURE:
<221> NAME/KEY: mat_peptide
<222> LOCATION: (785)...(2049)
<221> NAME/KEY: sig_peptide
<222> LOCATION: (55)...(784)
<221> NAME/KEY: intron
<222> LOCATION: (364)...(415)
<221> NAME/KEY: intron
<222> LOCATION: (802)...(854)
<221> NAME/KEY: intron
<222> LOCATION: (1821)...(1868)

<400> SEQUENCE: 1

```
atgcgtttct ccgactctct cctcctcatc ggcctatcca gcctcgctgg tgctcatccc      60
agcagaaggg ctcctaatcc ttcaccgctg agcaagcgtg gcctcgacct ggaagctttt     120
aagcttcctc ccatggccga gtacgttcct caggacgagg ttcctgatga tgtcagtgcc     180
aaggtcgtca ccaagcgcgc tgattacacc gagactgcca aggacttggt taagtcgact     240
ttccccaagg ctactttccg tatggtcacg gatcactatg ttggtagcaa cggaattgcg     300
catgtaaact ttaagcagac tgtcaacggt attgatatcg acaatgctga tttcaacgtc     360
aacgtgggta ttctcaagac tttggggagt ttggaatgtg ctgacatgga tacagattgg     420
cgctgacggc gaggtcttct cctacggaaa cagcttctac gagggcaaga ttcccggtcc     480
tcttaccaag cgtgacgaga agacccccgt cgacgctctc aaggacaccg ttgatgttct     540
ttctctcccc gttgaggctg acaaggccaa ggctgagaag aagagcaaga accactacac     600
```

-continued

| | |
|---|---|
| cttcactggt accaagggta ccgtcagcaa gcccgaggct aagctcacct accttgttga | 660 |
| tgagaacaag gagctcaagc tcacatggag agttgagact gatattgttg caactggct | 720 |
| gttgacttat gtcaatgctg ccaagactga tgaggttgtt ggtgttgttg actacgtcaa | 780 |
| tgaggcgaca tacaaggtct agtacgtatt ccataaatt gacgattggg aaagaattga | 840 |
| ccgttgtatt atagtccttg gggtgtcaat gatccctcca agggatctcg ctccactgtt | 900 |
| gagaacccct ggaatctcgc ggcctccgag ttcacctggc tcagcgacgg ctcaaacaac | 960 |
| tacaccacaa cccgcgggaa caatggaatt gcacaggtga atccttcagg gggctccacg | 1020 |
| tatctgaaca attaccgtcc tgatagcccg tcgctgaagt tcgagtatga ttactccacc | 1080 |
| agcaccacta cacccaccac ctaccgcgat gcttccatcg ctcagctttt ctacacagcc | 1140 |
| aacaagtacc acgacctcct ctaccttctt ggctttaccg aacaggctgg taacttccag | 1200 |
| accaacaaca atggccaggg tggtgtagga acgatatgg ttatcctcaa cgctcaggac | 1260 |
| ggaagcggca ccaacaacgc caacttcgct acacccgctg acggtcagcc cggccgcatg | 1320 |
| cgaatgtatc tctggacata cagcacaccc cagcgtgact gcagtttcga cgctggcgtt | 1380 |
| gttatccacg agtacactca cggtctctcc aaccgtctca caggtggccc tgccaactcg | 1440 |
| ggttgtcttc ccggtggtga atccggtggc atgggtgagg ctggggtga cttcatggct | 1500 |
| actgccattc acatccaatc caaggatacc cgcgctagca caaggtcat gggtgactgg | 1560 |
| gtgtacaaca acgcagctgg tatccgagct tatccttaca gtacaagcct taccactaac | 1620 |
| ccttacactt acaagagtgt taacagtctc agtggagtcc atgctattgg tacttactgg | 1680 |
| gctactgttc tgtatgaggt tatgtggaac ctcatcgaca agcatgggaa gaatgatgcg | 1740 |
| gatgagccca aattcaacaa cggcgttcct acagatggca aatatcttgc tatgaagtta | 1800 |
| gtagtggatg gcatgtcgct gtaagttgtc ccttggattt gtaggagttc ttatctaacg | 1860 |
| tttaataggc aaccttgcaa ccccaacatg gtccaggccc gagacgccat catcgacgcc | 1920 |
| gacaccgctc ttaccaaggg agctaacaag tgcgagatct ggaagggctt gccaagcgt | 1980 |
| ggtcttggaa ctggtgccaa gtatagtgct ccagccgta ctgagagctt tgctcttcct | 2040 |
| tctggatgtt aa | 2052 |

```
<210> SEQ ID NO 2
<211> LENGTH: 2968
<212> TYPE: DNA
<213> ORGANISM: Aspergillus oryzae
<220> FEATURE:
<221> NAME/KEY: exon
<222> LOCATION: (458)...(817)
<221> NAME/KEY: exon
<222> LOCATION: (868)...(1262)
<221> NAME/KEY: exon
<222> LOCATION: (1320)...(1870)
<221> NAME/KEY: exon
<222> LOCATION: (1930)...(2344)
<221> NAME/KEY: exon
<222> LOCATION: (2404)...(2587)

<400> SEQUENCE: 2
```

| | |
|---|---|
| cccccgattg ggaagacctt gaatccaatc tatcggagag ccgacggaac gggttttctt | 60 |
| gaacccaatg tcccaattgc tttgagaaaa tggatattat tcaatgcccc tgatcattat | 120 |
| tggcatactc ttcacggagt ggtctgcccc tgggcgattg ctccaccatg aggtgcatga | 180 |
| aggtaacccc gagctgctat agatgaagtg tgtcggatat tgcaggagtc tgaatgcgca | 240 |
| gctgattgcc cttttcccac catgatgaat gggacacaat atgtctagct ccgggttgtc | 300 |

-continued

| | |
|---|---|
| tcgggccaag aagaaatgct tctttgcgtt gatccagcgc gtcgaaatct ccaattgaac | 360 |
| cggtataaat aacagctgag cgtcgcagca ttcaaggcag aaccattcca cagatcatct | 420 |
| tctatcattt gcattgagtc caacgccctg gcagttcatg atgcggggtc ttctactagc | 480 |
| tggagccctt ggcctacctt tggccgtcct tgcgcatccg acccatcatg cacatggact | 540 |
| tcaacgtcgc acagttgact tgaactcatt ccgtttgcac caggcagcga agtatatcaa | 600 |
| tgcgactgag tcttcgagtg atgtttcatc ttctttctct cccttcaccg agcaaagcta | 660 |
| cgtggagacg gccactcagc tcgtgaagaa tatcctgcca gatgctacct tccgtgtcgt | 720 |
| caaggatcat tacattggta gcaatggggt cgctcatgtc aattttcgtc agacggtcca | 780 |
| tggccttgac attgacaatg cggacttcaa tgtcaatgta cgctgcagtc cacctatact | 840 |
| atgttcggtg ctaaccactt catttaggtt gggaaaaatg gaaagatctt ttcctatggc | 900 |
| cactcatttt atacgggcaa atccccgat gccaatcctt tgacgaagcg ggattatacc | 960 |
| gaccctgtag cggctctcag aggaaccaac gaagctttac agctttctat cactctagat | 1020 |
| caagtgtcta ctgaggctac cgaggacaaa gagtccttca atttcaaggg agtctctggc | 1080 |
| accgtttcgg atcccaaggc tcagttggtc tacttggtaa aggaagatgg cagccttgct | 1140 |
| ttgacctgga aggtggagac agatattgac agcaactggc tgttgaccta catcgatgcc | 1200 |
| aataccggca aagatgtcca tggtgtggtt gactacgtag ccgaggcaga ttaccaagta | 1260 |
| tagtgagtat tttaagaatg tgacttggac tgtagaatga agctgacaca ccaccacagt | 1320 |
| gcatgggta ttaatgatcc cacggagggc cctcgcaccg tcatcagcga tccatgggat | 1380 |
| tcgtccgcat ctgcgttcac ctggatcagt gacggagaaa acaactatac cacaactcgc | 1440 |
| ggcaacaacg gtatcgcgca gtcgaaccct accggtggat cgcagtactt gaagaactac | 1500 |
| cggcctgata gccccgattt gaaattccaa taccctatt cgctcaacgc cacaccccca | 1560 |
| gagtcctata ttgatgcgtc tatcactcag cttttctaca ctgccaacac gtaccacgac | 1620 |
| ctactctaca ctctgggctt caacgaggag gccggtaatt ccagtacga taacaatgga | 1680 |
| aaaggaggtg ctgaaacga ctacgtgatc ctcaatgctc aggacggttc tggcaccaat | 1740 |
| aacgccaact tcgctacgcc cccggatgga cagcccggcc gcatgcgcat gtacatttgg | 1800 |
| accgagtccc agccttaccg tgacggctcc ttcgaggctg gtattgtgat tcacgagtat | 1860 |
| actcacggtc gtatgtatcc cttatgaacc ccaagataag gcagtctgaa ctaacaccat | 1920 |
| ggtacacagt ctctaaccgg ctcactggag gacctgctaa ctctcgctgc ttgaatgccc | 1980 |
| ttgaatccgg cggaatgggt gaaggttggg gagacttcat ggccacggca attcggctca | 2040 |
| aggccggcga tactcactcg accgattata ccatgggtga atgggctgca aacaagaaag | 2100 |
| gtggcatccg tgcttaccca ttctcaacct ccctggaaac caaccctctc acctacacca | 2160 |
| gtctcaatga attggacgaa gtgcatgcca tcggcgcggt gtgggctaac gtattgtacg | 2220 |
| agctgttgtg gaacttgatc gataagcacg gcaagaatga cgggccaaag cccgagttca | 2280 |
| aggatggagt tccgactgac ggcaagtatc tcgccatgaa gctggtgatt gatggcatag | 2340 |
| cattgtaagt gccaacctcg tttcctcttt ctacctatcg caggggctaa ccttgacttt | 2400 |
| taggcaacct tgcaacccca actgtgtcca ggctcgcgac gccatcctcg atgccgataa | 2460 |
| ggctctcacc gatggtgcta acaagtgcga gatttggaag gcgtttgcta agcgtggttt | 2520 |
| gggtgaaggc gctgaatacc atgcgtctcg tcggtgggc agtgataagg tgccctctga | 2580 |
| tgcttgctag agtttgtgta tattctttca gctaggtgat tggggagatc ctgtaggctg | 2640 |
| actatagttt gaatttaaca acatttctta attcttactg tcaggtaact tgcactgcac | 2700 |

-continued

```
aatagcatga ataggttatg gcactctggc ccttatgtcg gatttctaca caatgatttg     2760
tccttaagaa atactatctc aactcatcac ccctctcatc gtccgccgct tcgaattcag     2820
ggtcattctt ccccgtcttc ctggccccct tggccgtcct gaccctctgc ttgctctcca     2880 tctcccctc cacctgatc ataggtcacg gtggccgccg tcccaccag gtggttgggg       2940 caatagttgt ttatagcacg gggctgct                                        2968

<210> SEQ ID NO 3
<211> LENGTH: 3922
<212> TYPE: DNA
<213> ORGANISM: Aspergillus oryzae
<220> FEATURE:
<221> NAME/KEY: exon
<222> LOCATION: (2310)...(2634)
<221> NAME/KEY: exon
<222> LOCATION: (2684)...(3129)
<221> NAME/KEY: exon
<222> LOCATION: (3188)...(3276)
<221> NAME/KEY: exon
<222> LOCATION: (3333)...(3686)

<400> SEQUENCE: 3
ggatccataa tgagcacact tgaacctcgc atgagtgctc catatcttag atccatttga      60
gtcacgagcg tcgaagccaa ggctaaaaga aagggacca agaccgccgc atatcggggt     120
ggctgaacaa tcgctgctag tgtgtacaca ggatacataa attaatcaag agccaatgac    180
gttatcgaag acatgatatt acttacttga tttgttgcgg tgctccgact caactggatt    240
cagatggaag ggaagggatt cttgatcagg ctcgtcccgg gatgaccatt gctcctctcg    300
aatcgagaca atgttgaatg cccaggatga cgattgagag cgagatatta aaaagagat    360 taagggttga cgattgccaa cggaagcccg atggaagaag aaatgccaag aatttggctg    420
cctggatgtt agtgccgttt agcctcaggc cccagctgaa tccctgccaa tcacgaggca    480
gggctcacca cctccaaccc ttacacaaga ctcgccctcg ctctttcctg caggtcctct    540
gcttactttc ccctctttc cctcctgaaa tgccccgaga atgccgtccg agcttagga      600 aagctacgac ggcttaatgt tctaatttcc cccaccgacc tgccctggcc agttagaccg    660 ccggaccat cgaatgcaac atcaccaaca ctaatttacc tgcatctctg tcagcccact     720
gggtttaact agatatgcca aggacttgct tggctggttt atgcatgaag agagatgggc    780
actagtgcgt gcgggaccac aaaccctcac tgcagagggc tcatgcacct gaaagactgc    840
caatgatcat ttgactggtt aggtcaaggg gttaggctta gagcccttg ctaatgccga     900 tgccgcctct ttgactgcca catttcttgg cttcccctct tggcccctcc cgtcccttga    960
tgccaagggc cttggtggct cggactcccg gcggtaggct ggccacctac tcatggcgtg   1020
cggagatggg ccattcaggt tgtgcctaat gacatactct gatgccgacg ggaaggccgg   1080
ctgcttgctg gtgtcattgg cttctcgaat gactcggagg attgtcgtct tgcaggactt   1140
ttgtgtaaca acaggggccg acagttggcg tggctgccgt ggatatgctt ttgctgcgag   1200
ccatggttat tctgcggaac gaaaccaccc tcccacccaa acagggctaa tgtgcccagg   1260
tcctgatacc atcagaagac ctccaggagc acatgcctgt tcgcataacc gtggtgtagc   1320
accaggaatt gcttagctta gcttcttcga ctgggggggcc agaaagtgct tatcgcaaag   1380
atcccacttc tttgtgtgat agccctcccc gcggcccttg atcaagccgt tctcgctcgc   1440
ccataccgaa accgcgatat tataggtgca gatggttatt attctttttc tttttctttt   1500
tctttgcttc tcatgcagcc ccatacgttg ccgaatttgg ctacaccttg gggctcattc   1560
```

-continued

```
ttcgaagttt agattccgac aagacctcag cacccaatca aaaccctcga ttcctgataa    1620
aagacgtgga aaaaagcgga tatcgcgtga ggatgccaag caaagggaat gggtcacatt    1680
gatctctgtc gcgctgttag gatgatcttc actcctaaag gcatcgccgc ggcattaggc    1740
ccttccctgt ccaagatatc ggttactcct ctcattatgg cgagctactt tgtgaattaa    1800
ttgactgagg gatataccac cttcccttg aaggtaccga gccactacct tgagcgttag     1860 ttacttttc gaggaaagca tcctatgcta gtctctgcca atcactgcag cgtcgacaac      1920
ttgccatagc cttgtgttct tcacggtcta tcggaacacc cgttcatgac tgaaaggggt    1980
cagcgtccgt ggtggtcaac atcattctca tctttcatca tgcccgctga ttgatagagt    2040
aatttccggt ggagcacaac gccgtcctct gagatgcaat gtcaccctgt aagtttcaac    2100
tacaatctgt agtacagagc atccttgtac ttgcatgctg tgcaagtgat ccaaatccgt    2160
agaacttgct cgagaacagg gaaatataga actcctgaag gttataaata ccacatgcat    2220
ccctcgtcca tcctcacttc catcatcaag ccagcggttt ctatcctccg acttgagttg    2280
ttcttgcgca tctttacaat cttctcatca tgcagtccat caagcgtacc ttgctcctcc    2340
tcggagctat ccttcccgcg gtcctcggtg ccctgtgca ggaaacccgc cgggccgctg     2400
agaagcttcc tggaaagtac attgtcacat tcaagcccgg cattgacgag gcaaagattc    2460
aggagcatac cacctgggct accaacattc accagcgcag tctggagcgt cgtggcgcca    2520
ctggcggtga tcttcctgtc ggtattgagc gcaactacaa gatcaacaag ttcgccgcct    2580
atgcaggctc tttcgacgat gctaccattg aggagattcg caagaacgaa gatgtttgtg    2640
gtcatccgct cgcatttttg aatgacagct aactcgcgcc caggttgcct acgtcgagga    2700
ggaccagatc tactacctcg atggcctgac tacccagaag agtgcccct ggggtctggg     2760 cagcatttcc cacaagggcc agcagagcac cgactacatc tacgacacta gtgccggcga    2820
gggcacctat gcctacgtgg tggatagcgg tgtcaatgtc gaccatgagg agttcgaggg    2880
ccgcgccagc aaggcctaca cgctgccgg tggtcagcat gtggacagca ttggccatgg    2940
cacccacgtt tccggcacca ttgctggcaa gacttatggt atcgccaaga aggccagcat   3000
cctttcggtc aaagttttcc agggtgaatc gagcagcact tccgtcattc ttgacggctt   3060
caactgggct gccaacgaca ttgttagcaa gaagcgtacc agcaaggctg caatcaacat    3120
gagcttgggt gagtttacat tgttcttctc tacttggaac gcgcgagcgc taatttcaaa    3180
aacacaggcg gtggctactc taaggctttc aacgatgcgg tcgagaacgc attcgagcag    3240
ggtgttctct cggttgtcgc tgccggtaac gagaacgtac gtctcccctc catcgcgcaa    3300
agacgaattc gtaactgact tgattttctt agtctgatgc cggccaaacc agccctgcct    3360
ctgcccctga tgccatcact gttgccgcta tccagaagag caacaaccgc gccagtttct    3420
ccaactttgg caaggtcgtt gacgtcttcg ctcccggtca agatatcctt tctgcctgga    3480
ttggctcttc ctctgccacc aacaccatct ctggtacctc catggctact ccccacattg    3540
tcggcctgtc cctctacctc gctgcccttg agaacctcga tggccccgct gccgtgacca    3600
agcgcatcaa ggagttggcc accaaggacg tcgtcaagga tgttaagggc agccctaacc    3660
tgcttgccta caacggtaac gcttaagtac caggagtacg tcgcaggatt ctaccattgt    3720
tactggaata caatgatgat tagaaaacga agagcgttat gattcggacg gatatatgca    3780
tggcacccat acagcgtgat acataggctg tttgctcaag aattaggatt ttatctgaat    3840
ccatgtacag agtatactta tgttagtagt caataaaatc ttggctttct aattttgtcc    3900
```

-continued

```
catctacaag gggtcgtcga tc                                      3922

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
ccctcgggct cggaccccgc cttctcgcag cccaag                         36

<210> SEQ ID NO 5
<211> LENGTH: 41
<212> TYPE: DNA
<213> ORGANISM: Artificial Sequence
<220> FEATURE:
<223> OTHER INFORMATION: Primer

<400> SEQUENCE: 5
ccctcgttcg tcaggcccgc gtccagcacc gacttgggct g                   41

<210> SEQ ID NO 6
<211> LENGTH: 1029
<212> TYPE: DNA
<213> ORGANISM: Candida antarctica

<400> SEQUENCE: 6
atgaagctac tctctctgac cggtgtggct ggtgtgcttg cgacttgcgt tgcagccact   60
cctttggtga agcgtctacc ttccggttcg gaccctgcct tttcgcagcc caagtcggtg  120
ctcgatgcgg gtctgacctg ccagggtgct tcgccatcct cggtctccaa acccatcctt  180
ctcgtccccg gaaccggcac cacaggtcca cagtcgttcg actcgaactg gatcccctc   240 tcaacgcagt tgggttacac accctgctgg atctcacccc cgccgttcat gctcaacgac  300
acccaggtca cacggagta catggtcaac gccatcaccg cgctctacgc tggttcgggc   360
aacaacaagc ttcccgtgct tacctggtcc cagggtggtc tggttgcaca gtggggtctg  420
accttcttcc ccagtatcag gtccaaggtc gatcgactta tggcctttgc gcccgactac  480
aagggcaccg tcctcgccgg ccctctcgat gcactcgcgg ttagtgcacc ctccgtatgg  540
cagcaaacca ccggttcggc actcaccacc gcactccgaa acgcaggtgg tctgacccag  600
atcgtgccca ccaccaacct ctactcggcg accgacgaga tcgttcagcc tcaggtgtcc  660
aactcgccac tcgactcatc ctacctcttc aacggaaaga acgtccaggc acaggccgtg  720
tgtgggccgc tgttcgtcat cgaccatgca ggctcgctca cctcgcagtt ctcctacgtc  780
gtcggtcgat ccgccctgcg ctccaccacg ggccaggctc gtagtgcaga ctatggcatt  840
acggactgca accctcttcc cgccaatgat ctgactcccg agcaaaaggt cgccgcggct  900
gcgctcctgg cgccggcagc tgcagccatc gtggcgggtc caaagcagaa ctgcgagccc  960
gacctcatgc cctacgcccg cccctttgca gtaggcaaaa ggacctgctc cggcatcgtc 1020
acccctga                                                         1029
```

HOST CELLS AND METHODS OF PRODUCING PROTEINS

CROSS-REFERENCE TO RELATED APPLICATIONS

This application is a continuation application of PCT/DK97/00397 filed on Sep. 19, 1997 and claims priority under 35 U.S.C. 119 of Danish application 0124/96 filed on Sep. 19, 1996, the contents of which are fully incorporated herein by reference.

FIELD OF THE INVENTION

The present invention relates to novel fungal host cells and to methods of producing proteins. More specifically, the invention relates to a host cell useful for the expression of heterologous proteins in which the host cell has been genetically modified in order to express significantly reduced levels of a metalloprotease and an alkaline protease. Moreover, the invention relates to a method of producing proteins of interest in high yields by using the fungi of the invention, in which the method comprises cultivating the host cell in a suitable growth medium, followed by recovery of the desired protein. The invention also comprises methods for producing such fungi and DNA constructs to be used in these methods.

BACKGROUND OF THE INVENTION

The use of recombinant host cells in the expression of heterologous proteins has in recent years greatly simplified the production of large quantities of commercially valuable proteins which otherwise are obtainable only by purification from their native sources. Currently, there is a varied selection of expression systems from which to choose for the production of any given protein, including eubacterial and eukaryotic hosts. The selection of an appropriate expression system often depends not only on the ability of the host cell to produce adequate yields of the protein in an active state, but, to a large extent, may also be governed by the intended end use of the protein.

One problem frequently encountered is the high level of proteolytic enzymes produced by a given host cell or present in the culture medium. It has been suggested that one could provide host organisms deprived of the ability to produce specific proteolytic compounds. For example, International Patent Application WO 90/00192 (Genencor) describes filamentous fungal hosts incapable of secreting enzymatically active aspartic proteinase, and EP 574 347 (Ciba Geigy AG) describes Aspergillus hosts defective in a serine protease of the subtilisin-type.

Metalloproteases have been isolated from a number of eukaryotic sources. Neutral metalloproteases, i.e. metalloproteases having optimal activity at neutral pH, isolated from strains of Aspergillus also have been reported. The physicochemical properties of two neutral metalloproteases from *Aspergillus sojae*, NpI and NpII, have been reported in a series of studies (Sekine, H. 1972. Agric. Biol. Chem. 36:198–206, 207–216; Sekine, H. 1972. Agric. Biol. Chem. 36:2143–2150). It was revealed that the enzymatic and physicochemical characteristics of NpI, but not Np II, resemble those of *Bacillus thermoproteolyticus* thermolysin. Recently, the cDNA sequence of a neutral metalloprotease, NpII, from *Aspergillus oryzae* was disclosed (Tatsumi H, et al. 1991. Mol. Gen. Genet. 228:97–103). However, the cDNA sequence of a neutral metalloprotease from the NpI group from *Aspergillus oryzae* has never been disclosed.

Alkaline protease is a serine protease with an alkaline pH optimum (Nakagawa, Y. 1970. Methods Enzymol. 19:581–591). It is a homologue of subtilisin and is the predominant extracellular alkaline endopeptidase of *Aspergillus oryzae*. The gene has been isolated and characterised (Murakami, et al. 1991. Agric. Biol. Chem. 55:2807–2811). Two other species of Aspergillus, *A. flavus* and *A. sojae*, produce identical or closely related enzymes.

A potential role of metalloproteases and alkaline proteases in reducing the stability of protein products obtained from Aspergillus has not been reported.

SUMMARY OF THE INVENTION

According to the present invention it has now been found that the proteolytic activity of neutral metalloprotease I and alkaline protease, either individually or in combination, may significantly reduce the stability of a protein product of interest produced by a cell resulting in a reduced yield of the said protein.

Accordingly, the present invention provides a host cell useful for the expression of a heterologous protein product, in which the cell has been genetically modified in order to express significantly reduced levels of both a metalloprotease and an alkaline protease, by comparison to the parental cell.

In another aspect, the invention provides a method of producing a heterologous protein product in a host cell of the invention, in which the method comprises introducing into the host cell a nucleic acid sequence encoding the protein, cultivating the host cell in a suitable growth medium, and recovering the heterologous protein product.

By the method of the invention, proteolytic activity resulting from a neutral metalloprotease I and an alkaline protease are significantly reduced, thereby improving the stability and yield of the protein obtained by the method. Moreover, the protein obtained by the method of the invention may be a precursor protein such as a zymogen, a hybrid protein, a protein obtained as a pro sequence or pre-pro sequence, or any other type of immature form.

BRIEF DESCRIPTION OF THE DRAWINGS

The present invention is further illustrated by reference to the accompanying drawings, in which.

DETAILED DISCLOSURE OF THE INVENTION

Host Cells

Figure 1:
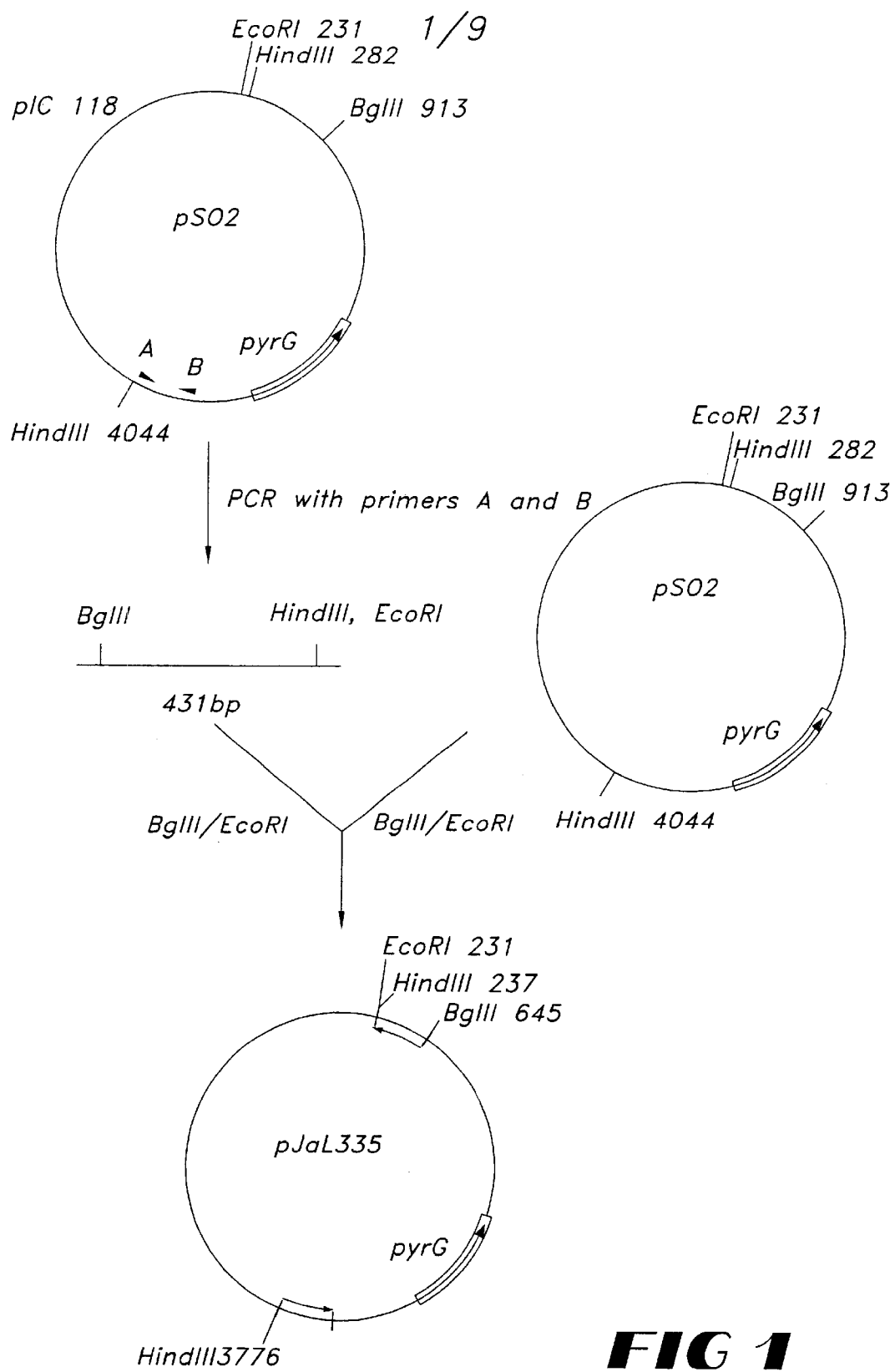
FIG. 1 diagrams the construction of the plasmid pJaL335 which harbours the pyrG gene.

The present invention provides a host cell useful for the expression of heterologous proteins, wherein the cell has been genetically modified in order to express significantly reduced levels of metalloprotease and alkaline protease activity in comparison to a parental cell. Said host cell is derived from the parental cell which may be a wild type cell.

The host cell of the invention may be any host cell conventionally used for the heterologous expression of proteins.

Preferably, the host cell of the invention is a yeast or a filamentous fungus capable of producing a desired protein. In particular, the yeast cell may be a strain of Saccharomyces, preferably *Saccharomyces cerevisiae*. In particular, the filamentous fungus may be a strain selected from the group consisting of Acremonium, Aspergillus, Candida, Cocliobolus, Endothia, Fusarium, Humicola, Neurospora, Rhizomucor, Rhizopus, Thermomyces, Trichoderma, Podospora, Pyricularia, and Penicillium.

In a preferred embodiment, the filamentous fungus is a strain selected from the group consisting of *Aspergillus nidulans, Aspergillus awamori, Aspergillus phoenicis, Aspergillus japonicus, Aspergillus foetus, Fusarium graminearum, Fusarium oxysporum, Fusarium solani, Fusarium venenatum, Humicola grisea, Neurospora crassa, Penicillium chrysogenum, Rhizomucor meihei, Trichoderma reesei,* and *Trichoderma viride*; in particular, a strain of *Aspergillus oryzae, Aspergillus niger* and Fusarium species having the identifying characteristics of ATCC 20334.

Metalloproteases

In the context of this invention, a metalloprotease is a proteolytic enzyme containing a catalytic zinc metal center which participates in the hydrolysis of the peptide backbone of the substrate. The active zinc centre differentiates these proteases from the calpains, whose activities are dependent upon the presence of calcium. Confirmation of a protease as a metalloprotease is by the reversible loss of proteolytic activity upon removal of the zinc centre with 1 mM 1,10-phenanthroline, and its restoration after titration with $Zn^{2+}$ (0.1–100 mM).

In a preferred embodiment, the metalloprotease contemplated in the context of this invention is a Fusarium metalloprotease, preferably a *Fusarium oxysporum* metalloprotease. In a most preferred embodiment, the metalloprotease is a *Fusarium oxysporum* p45 metalloprotease (p45) having the nucleotide sequence presented as SEQ. ID. No. 1, or a sequence homologous thereto.

In another preferred embodiment, the metalloprotease contemplated in the context of this invention is a neutral metalloprotease, which is a metalloprotease possessing optimal proteolytic activity in the neutral pH region, i.e. in the range of about pH 6–8, preferably in the range of about pH 6.5–7.5, more specifically, around pH 7. More particularly, the metalloprotease contemplated in the context of this invention is a neutral Aspergillus metalloprotease of the group NpI or NpII (Tatsumi, et al., 1991, supra).

In a preferred embodiment, the metalloprotease is an *Aspergillus oryzae* neutral Metalloprotease I (NpI) comprising an amino acid sequence derived from the nucleotide sequence presented as SEQ. ID. No. 2, or a sequence homologous thereto.

Alkaline proteases

In the context of this invention an alkaline protease is a serine protease with activity which peaks in the neutral to alkaline pH range. Analyses of the amino acid sequence of alkaline proteases indicate homology to the subtilase subgroup of subtilisin-like serine proteases. As summarised by Siezen, et al. (1991. Protein Eng. 4:719–737) more than 50 subtilases have been identified from a wide variety of organisms, ranging from various species of bacteria, including gram positive and gram negative species, to fungi and yeast to higher eukaryotes, including worms, insects, plants and mammals. The amino acid sequence has been determined in more than 40 of these subtilases, and reveal that the mature region of the enzyme ranges from 268 to 1775 amino acids in length and a pre-pro-region of 27 to 280 amino acids in the N-terminal vicinity. In fungi and yeast, the variation is apparently smaller, with corresponding ranges of 279 to 281 and 105 to 121 in fungi, and 297 to 677 and 126 to 280 in yeast. A cDNA fragment of the entire coding region of the alkaline protease from *Aspergillus oryzae* was cloned and expressed in *Saccharomyces cerevisiae* (Tatsumi, H, et al. 1989. Mol. Gen. Genet. 219:33–38). The primary structure was shown to share 29% to 44% homology with other sequenced subtilisins, and the three residues in the active site, Asp32, His 64 and Ser221 in subtilisin BPN', were conserved.

In a preferred embodiment, the alkaline protease is an *Aspergillus oryzae* alkaline protease (alp), preferably encoded by a cDNA sequence comprising the nucleotide sequence presented as SEQ. ID. No. 3, or a sequence homologous thereto.

Sequence Homology

As used herein DNA sequence homology is determined as the degree of identity between the two sequences indicating a derivation of the first sequence from the second. The homology may be suitably determined by means of computer programs well known in the art, such as GAP, provided in the GCG program package (Program Manual for the Wisconsin Package, Version 8, August 1994, Genetics Computer Group, 575 Science Drive, Madison Wis., USA; Needleman, S. B. and Wunsch, C. D., 1970. J. Mol. Biol. 48:443–453). Using the following GAP settings for DNA sequence comparison, a creation penalty of 5.0 and an extension penalty of 0.3, the coding region of the analogous DNA sequence exhibits a degree of identity preferably of at least 70%, more preferably at least 80%, more preferably at least 90%, more preferably at least 95%, and most preferably at least 97% with the encoding region of an indicated DNA sequence.

Amino acid sequence homology as used herein is similarly determined as the degree of identity between two sequences indicating a derivation of the first sequence from the second. The homology may be suitably determined by means of computer programs well known in the art, such as GAP referred to above (Needleman, S. B. and Wunsch, C. D., 1970, supra). Using GAP with the following settings for amino acid sequence comparison, a creation penalty of 3.0 and extension penalty of 0.1, the polypeptide encoded by an analogous DNA sequence exhibits a degree of identity preferably of at least 70%, more preferably at least 80%, more preferably at least 90%, more preferably at least 95%, especially at least 97% with a DNA sequence comprising the region encoding the structural protein.

The present invention is also directed to variants of metalloproteases and alkaline proteases teases which have an amino acid sequence differing by no more than three amino acids, preferably by no more than two amino acids, and more preferably by no more than one amino acid from the mature polypeptide of the amino acid sequence derived from SEQ. ID. No. 1, SEQ. ID No. 2 and SEQ. ID. No. 3.

Hybridisation as used herein is intended to indicate that an analogous DNA sequence binds to an oligonucleotide probe corresponding to a polypeptide encoded by an indicated DNA sequence comprising the region encoding the structural protein under certain specified conditions which are described in detail below.

Suitable conditions for determining hybridization between a nucleotide probe and a homologous DNA or RNA sequence involves presoaking the filter containing the DNA fragments or RNA to be hybridized in 5×SSC (standard saline citrate buffer; cf, Sambrook et al., 1989. *Molecular Cloning*, Cold Spring Harbor N.Y., USA) for 10 min, and prehybridization of the filter in a solution of 5×SSC, 5×Denhardt's solution, 0.5% SDS and 100 μg/ml of denatured sonicated salmon sperm DNA (Sambrook et al. 1989, supra), followed by hybridization in the same solution containing a random-primed (Feinberg, A. P., and Vogelstein, B. 1983. Anal. Biochem. 132:6–13), $^{32}$P-dCTP-labeled (specific activity>1×10$^9$ cpm/μg) probe for 12 hours at ca. 45° C. The filter is then washed two times for 30 minutes in 2×SSC, 0.5% SDS at a temperature of at least 55° C. (low stringency), more preferably at least 60° C. (medium stringency), more preferably at least 65° C. (medium/high stringency), more preferably at least 70° C. (high stringency), even more preferably at least 75° C. (very high stringency). Molecules to which the oligonucleotide probe hybridise under these conditions are detected by exposure to x-ray film.

Genetic Modifications of the Host Cell

The host cell of the invention, in order to express significantly reduced levels of metalloprotease and alkaline protease activity, is genetically modified which may be achieved by using standard recombinant DNA technology known to the person skilled in the art. The gene sequences respectively responsible for production of metalloprotease and alkaline protease activity may be inactivated or partially or entirely eliminated. Thus, a host cell of the invention expresses reduced or undetectable levels of metalloprotease and alkaline protease or expresses functionally inactive metalloprotease and alkaline protease.

In a particular embodiment, the said inactivation is obtained by modification of the respective structural or regulatory regions encoded within the metalloprotease and alkaline protease genes of interest. Known and useful techniques include, but are not limited to, specific or random mutagenesis, PCR generated mutagenesis, site specific DNA deletion, insertion and/or substitution, gene disruption or gene replacement, anti-sense techniques, or a combination thereof.

Mutagenesis may be performed using a suitable physical or chemical mutagenising agent. Examples of a physical or chemical mutagenising agent suitable for the present purpose include, but are not limited to, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulfite, formic acid, and nucleotide analogues. When such agents are used, the mutagenesis is typically performed by incubating the cell to be mutagenised in the presence of the mutagenising agent of choice under suitable conditions, and selecting for cells showing a significantly reduced production of NpI and alp.

Modification may also be accomplished by the introduction, substitution or removal of one or more nucleotides in the structural sequence or a regulatory element required for the transcription or translation of the structural sequence. For example, nucleotides may be inserted or removed so as to result in the introduction of a stop codon, the removal of the start codon or a change of the open reading frame of the structural sequence. The modification or inactivation of the structural sequence or a regulatory element thereof may be accomplished by site-directed mutagenesis or PCR generated mutagenesis in accordance with methods known in the art. Although, in principle, the modification may be performed in vivo, i.e. directly on the cell expressing the metalloprotease and alkaline protease genes, it is presently preferred that the modification be performed in vitro as exemplified below.

A convenient way to inactivate or reduce the metalloprotease and alkaline protease production in a host cell of choice is based on techniques of gene interruption. In this method a DNA sequence corresponding to the endogenous gene or gene fragment of interest is mutagenised in vitro. Said DNA sequence thus encodes a defective gene which is then transformed into the host cell. By homologous recombination, the defective gene replaces the endogenous gene or gene fragment. It may be desirable that the defective gene or gene fragment also encodes a marker which may be used to select for transformants in which the respective genes encoding metalloprotease and/or alkaline protease have been modified or destroyed.

Methods for deleting or disrupting a targeted gene are specifically described by Miller, et al. (1985. Mol. Cell. Biol. 5:1714–1721); WO 90/00192; May, G. (1992. *Applied Molecular Genetics of Filamentous Fungi*. J. R. Kinghorn and G. Turner, eds., Blackie Academic and Professional, pp. 1–25); and Turner, G. (1994. *Vectors for Genetic Manipulation*. S. D. Martinelli and J. R. Kinghorn, eds., Elsevier, pp.641–665).

Alternatively, the modification or inactivation of the DNA sequence may be performed by established anti-sense techniques using a nucleotide sequence complementary to an encoding sequence for metalloprotease, e.g. the nucleotide sequences presented as SEQ. ID. No. 1 and SEQ. ID. No. 2, or an alkaline protease encoding sequence, e.g. the nucleotide sequence shown in SEQ. ID. No. 4. The anti-sense technology and its application is described in detail in U.S. Pat. No. 5,190,931 (University of New York).

Therefore, due to genetic modification, the host cell of the invention expresses significantly reduced levels of metalloprotease and alkaline protease activity. In a preferred embodiment, the level of these proteolytic activities expressed by the host cell is individually reduced more than about 50%, preferably more than about 85%, more preferably more than about 90%, and most preferably more than about 95%. In another preferred embodiment, the these proteolytic activities in the host cell of the invention may be reduced in any combination. In a most preferred embodiment, the product expressed by the host cell is essentially free from proteolytic activity due to metalloprotease and alkaline protease.

Methods of Producing Proteins

By the method of the invention, the proteolytic activities of metalloprotease and alkaline protease are significantly reduced, thereby improving the stability and increasing the yield of susceptible protein products synthesised by the host cell of the invention. More specifically, by the method of the invention, the host cell is genetically modified within structural and/or regulatory regions encoded within the metalloprotease and alkaline protease genes.

Therefore, another aspect of the invention provides a method of producing proteins in a host cell of the invention, including heterologous polypeptides, in which the method comprises introducing into said host cell a nucleic acid sequence encoding the protein product of interest, cultivating the host cell in a suitable growth medium, followed by recovery of the protein product.

Thus, the host cell of the invention must contain structural and regulatory genetic regions necessary for the expression of the desired product. The nature of such structural and regulatory regions greatly depends on the product and the host cell in question. The genetic design of the host cell of the invention may be accomplished by the person skilled in the art using standard recombinant DNA technology for the transformation or transfection of a host cell (vide, e.g., Sambrook et al., inter alia).

Preferably, the host cell is modified by methods known in the art for the introduction of an appropriate cloning vehicle, i.e. a plasmid or a vector, comprising a DNA fragment encoding the desired protein product. The cloning vehicle may be introduced into the host cell either as an autonomously replicating plasmid or integrated into the chromosome. Preferably, the cloning vehicle comprises one or more structural regions operably linked to one or more appropriate regulatory regions.

The structural regions are regions of nucleotide sequences encoding the desired protein product. The regulatory regions include promoter regions comprising transcription and translation control sequences, terminator regions comprising stop signals, and polyadenylation regions. The promoter, i.e. a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, an oxidoreductase, a pectinase, a cutinase, or a glycolytic enzyme. Examples of suitable promoters for transcription in a fungal host cell are promoters derived from the gene encoding *Aspergillus oryzae* TAKA amylase, *Aspergillus niger* neutral α-amylase, Aspergillus niger acid stable α-amylase, *Aspergillus niger* or *Aspergillus awamsii* glucoamylase (GluA), *Aspergillus nidulans* acetamidase, *Aspergillus oryzae* alkaline protease, *Aspergillus oryzae* triose phosphatase isomerase, *Rhizopus meihei* aspartic proteinase, and *Rhizopus meihei* lipase. Preferred promoters are the *Aspergillus oryzae* TAKA-amylase and *Aspergillus awamsii* GluA.

The cloning vehicle may also include a selectable marker, such as a gene product which complements a defect in the host cell, or one which confers antibiotic resistance. Examples of antibiotics useful as Aspergillus selection markers include hygromycin, phleomycin and basta. Other examples of Aspergillus selection markers include amdS, which encodes an enzyme involved in acetamide utilisation; pyrG, which encodes an enzyme involved in uridine biosynthesis; argB, which encodes an enzyme involved in arginine biosynthesis; niaD, which encodes an enzyme involved in the nitrate assimilation pathway; and sC, which encodes an enzyme involved in the sulfate assimilation pathway. Preferred for use in an Aspergillus host cell are the amdS and pyrG markers of *Aspergillus nidulans* or *Aspergillus oryzae*. Furthermore, selection may be accomplished by co-transformation, wherein the transformation is carried out with a mixture of two vectors and the selection is made for one vector only.

The procedures used to ligate the DNA construct of the invention, the promoter, terminator and other elements, respectively, and to insert them into suitable cloning vehicles containing the information necessary for replication, are well known to persons skilled in the art (vide e.g., Sambrook et al., 1989; inter alia).

The culture broth or medium used may be any conventional medium suitable for culturing the host cell of the invention, and formulated according to the principles of the prior art. The medium preferably contains carbon and nitrogen sources as well as other inorganic salts. Suitable media, e.g. minimal or complex media, are available from commercial suppliers, or may be prepared according to published recipes, as in *The Catalogue of Strains,* published by The American Type Culture Collection. Rockville Md., USA. 1970.

The appropriate pH for fermentation will often be dependent on such factors as the nature of the host cell to be used, the composition of the growth medium, the stability of the polypeptide of interest, and the like. Consequently, although the host cell of the invention may be cultured using any fermentation process performed at any pH, it is advantageous that the pH of the fermentation process is such that acidic and/or netural protease activities of the host cell are essentially eliminated or at least significantly reduced. Thus, removal of aspartic protease activity as described in WO 90/00192 may also be accomplished by raising the fermentation pH, and does not present any additional advantageous effect on the yield of a desired protein from host cells cultivated in the alkaline pH range.

If the pH of the fermentation process is within the range from 5 to 11, such as from 6 to 10.5, 7 to 10, or 8 to 9.5, the activity of acidic proteases, such as aspartic and serine proteases, and neutral proteases in the pH ranges above 7, will be reduced or blocked. Examples of enzymes produced under alkaline fermentation conditions include endoglucanases, phytases and protein disulfide isomerases.

However, the alkaline pH range will support alkaline protease activity in an unmodified host cell, which, in turn, may potentially result in degradation of the polypeptide product of interest. Consequently, in such cases the inactivation of the gene encoding alkaline protease is especially advantageous.

Inactivation of the alkaline protease gene of the invention is also especially advantageous for certain host cells, as the levels of acidic, neutral and alkaline protease activities vary from species to species. For example, the level of alkaline protease activity in the *Aspergillus oryzae* is higher than in *Aspergillus niger.*

After cultivation, the desired protein is recovered by conventional methods of protein isolation and purification from a culture broth. Well established purification procedures include separating the cells from the medium by centrifugation or filtration, precipitating proteinaceous components of the medium by means of a salt such as ammonium sulphate, and chromatographic methods such as ion exchange chromatography, gel filtration chromatography, affinity chromatography, and the like.

Products

The desired end product, i.e. the heterologous protein expressed by the host cell of the invention, may be any eubacterial or eukaryotic protein or peptide.

As defined herein, a "heterologous protein" is a protein or polypeptide gene product which is not native to the host cell, or is a native protein in which modifications have been made to alter the native sequence, or is a native protein whose expression is quantitatively altered as a result of a manipulation of a native regulatory sequence required for the expression of the native protein, such as a promoter, a ribosome binding site, etc., or other manipulation of the host cell by recombinant DNA techniques.

In a more specific embodiment, the product is a therapeutically active peptide or protein, such as a hormone, in particular insulin, growth hormone, glucagon, or somatostatin; an interleukin, in particular interferon; a haematopoietic growth factor, in particular PDGF (platelet derived growth factor), EPO (erythropoietin), or TPO (thrombopoietin); a protease, in particular factor VII, factor VIII, urokinase, chymosin, or tissue plasminogen activator; or serum albumin.

In another preferred embodiment, the product is an enzyme of fungal or of bacterial origin.

The enzyme is preferably a glycosidase enzyme, e.g. an amylase, in particular an α-amylase (EC 3.2.1.1) or a β-amylase (EC 3.2.1.2); a glucan 1,4-α-glucosidase (EC 3.2.1.3), a cellulase, in particular an endo-1,4-β-glucanase (EC 3.2.1.4) or an endo-1,3(4)-β-glucanase (EC 3.2.1.6); a xylanase, in particular an endo-1,4-β-xylanase (EC 3.2.1.8) or a xylan-endo-1,3-β-xylosidase (EC 3.2.1.32); a polygalacturonase (EC 3.2.1.15); a glucosidase, in particular an α-glucosidase (EC 3.2.1.20) or a β-glucosidase (EC 3.2.1.21); a galactosidae, in particular an α-galactosidase (EC 3.2.1.22) or a β-galactosidase (EC 3.2.1.23); an endoglucanase, in particular an endo-1,3-β-glucanase (EC 3.2.1.39), an endo-1,3-α-glucanase (EC 3.2.1.59), an endo-1,2-β-glucanase (EC 3.2.1.71), or an endo-1,6-β-glucanase (EC 3.2.1.75); and a cellulose-1,4-β-cellobiosidase (EC 3.2.1.91).

In another preferred embodiment the enzyme is a lipolytic enzyme, in particular a lipase, an esterase, a phospholipase, or a lyso-phospholipase.

In another preferred embodiment the enzyme is a phytase, in particular a 3-phytase (EC 3.1.3.8) or a 6-phytase (EC 3.1.3.26).

In another preferred embodiment the enzyme is a proteolytic enzyme.

In another preferred embodiment the enzyme is a laccase, a pectinase, or a cutinase, or an oxidoreductase, such as a peroxidase.

In another preferred embodiment the product is a hybrid polypeptide, preferably prochymosin and pro-trypsin-like proteases.

Due to the absence of metalloprotease and alkaline protease activities, the heterologous protein expressed by the host cell may also be a precursor protein such as a zymogen, a hybrid protein, a protein obtained as a pro sequence or pre-pro sequence, or any other immature form.

EXAMPLES

The invention is further illustrated with reference to the following examples which should not in any way be construed as limiting the scope of the invention as defined in the appended claims.

Materials and Methods

Strains

*Aspergillus oryzae* IFO 4177: available from Institute for Fermention, Osaka; 17–25 Juso Hammachi 2-Chome Yodogawaku, Osaka, Japan.

*Fusarium oxysporum* DSM 2672: deposited according to the Budapest Treaty on the International Recognition of the Deposit of Microorganisms for the Purposes of Patent Procedure at Deutsche Sammlung von Mikroorganismen und Zellkulturen GmbH (DSM), Mascheroder Weg 1b, DE-3300 Braunschweig, Germany, on Jun. 6, 1983.

HowB101: The construction of this strain is described in Example 1.

JaL125: The construction of this strain is described in Example 1.

JaL151: The construction of this strain is described in Example 1.

JaL228: The construction of this strain is described in Example 1.

Genes alp: This gene codes for the alkaline protease shown in SEQ. ID. No. 3.

NpI: This gene codes for the neutral metalloprotease I shown in SEQ. ID. No. 2.

pyrG: This gene codes for orotidine-5'-phosphate decarboxylase, an enzyme involved in the biosynthesis of uridine.

p45: This gene codes for the neutral metalloprotease I shown in SEQ. ID. No. 1.

Plasmids pSO2: The preparation is described in Example 1.
pSO5: The preparation is described in Example 1.
pSRe403: The preparation is described in Example 1.
SRe403ΔSacII: The preparation is described in Example 1.
pJaL173: The preparation is described in Example 1.
pJaL212: The preparation is described in Example 1.
pJaL335: The preparation is described in Example 1.
pJaL389: The preparation is described in Example 1.
pJaL399: The preparation is described in Example 1.
pToC65: The construction is described in EP 531 372 B.
pToC68: The construction is described in WO 91/17243.
pToC90: A subclone of p3SR2 (Corrick et al., 1987. GENE 53:63–71), harbouring the amdS gene from *Aspergillus nidulans* as a 2.7 kb XbaI fragment, on a pUC19 vector (Yannisch-Perron et al., 1985. GENE 33:103–119), this plasmid was prepared as described in WO 91/17243.
pDM115: The preparation is described in Example 1.
pMT1303: The preparation is described in Example 2.
pMT1305: The preparation is described in Example 2.
pMT1329: The preparation is described in Example 2.
pMT1330: The preparation is described in Example 2.
pMT1332: The preparation is described in Example 2.
pMT1335: The preparation is described in Example 2.

Proteolytic Enzyme Assays

Metalloprotease activity is measured as released trypsin activity after a 30–60 min preincubation at 25° C. in 0.1 M Tris, 2 mM $CaCl_2$, pH 7 (in the lower pH range a buffer of 100 mM borate, 10 mM DMG, 2 mM $CaCl_2$ is used). The tryptic activity is measured in microtiter plates; 100 ml samples are mixed with 100 ml of L-BAPNA substrate (a 50-fold dilution in buffer of the stock concentration of 87 mg/ml DMSO, Sigma Aldrich Corp., St. Louis Mo., USA) and the absorption at 405 nm is measured using a Thermomax microplate reader from Molecular Devices Corp. (Sunnyvale Calif., USA).

The alkaline protease activity is assayed at 25° C. using the synthetic substrate, N-succinyl-Ala-Ala-Pro-Phe-p-nitroanilide (Sigma Aldrich Corp.) at 1 mM in 20 mM Tris-HCl (pH 8.0) in a total reaction volume of 1 ml. The release of p-nitroanilin is monitored at 410 nm (Ramesh, Nev., et al. 1994. Infection and Immunity 62:79–85).

Example 1

Genomic Deletion of the *Aspergillus oryzae* Alkaline Protease (alp) Gene and the *Aspergillus oryzae* Neutral Metalloprotease I (NpI) Gene The alp and the NpI genes were each deleted by the one-step gene replacement method (Miller, B. L., et al., 1985. Mol. and Cell. Biol. 5:1714–1721, and May, G. in *Applied Molecular Genetics of Filamentous Fungi*, pp. 1–25. J. R. Kinghorn and G. Turner, eds.; Blackie Academic and Professional, 1992.) in two consecutive rounds in a pyrG⁻ strain of *A. oryzae*, using the *A. oryzae* pyrG gene as a selection marker.

Cloning of the *Aspergillus oryzae* pyrG Gene

The *A. oryzae* pyrG gene was cloned by cross-hybridization with the *A. niger* pyrG gene (van Hartingsveldt, W., et al., 1987. Mol. Gen. Genet. 206: 71–75). A lambda phage library from partially Sau3A digested *A. oryzae* IFO 4177 DNA was probed at low stringency with a 1 kb DNA fragment from the *A. niger* pyrG gene. DNA from one positive clone was subcloned into a pUC118 vector. The resultant plasmid, pSO2, was shown to contain the pyrG gene by complementation to an *A. niger* pyrG mutant.

Construction of pyrG Plasmid, pJaL335

A 431 bp fragment located 479 nucleotides upstream from the 5' end of the *A.oryzae* pyrG coding sequence was amplified by PCR, using the following two oligonucleotide primers:

Primer A:
5'-GGAGGAAGATCTCTCTGGTACTCTTCGATCT-C-3'; SEQ. ID. No. 4; and

Primer B:
5'-GGAGGAGAATTCAAGCTTCTTCTACATCACA-GTTTGAA AGC-3'; SEQ. ID. No. 5.

The underlined regions indicate sequences present in the 5' region of the *A. oryzae* pyrG gene. A restriction site was inserted into the 5' end of each primer to facilitate cloning; primer A contains a BglII site and primer B contains an EcoRI site adjacent to a HindIII restriction site.

Plasmid pSO2 was used as template in the PCR reaction. The reaction was performed in a volume of 100 μl containing 2.5 units Taq polymerase, 100 ng of pSO2, 250 nM of each dNTP, and 10 pmol of each of the two primers described above in a reaction buffer of 50 mM KCl, 10 mM Tris-HCl pH 8.0, 1.5 mM MgCl$_2$.

Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C. The PCR reaction produced a single DNA fragment of 430 bp in length. This fragment was digested with BglII and EcoRI and isolated by gel electrophoresis, purified, cloned into the corresponding site in plasmid pSO2, resulting in a plasmid which was called pJaL335. Thus, pJaL335 harbours the pyrG gene flanked by a 431 bp repeat. FIG. 1 summarises the steps in the construction of pJaL335.

Construction of a pyrG Deletion Plasmid, pSO5

Figure 2:
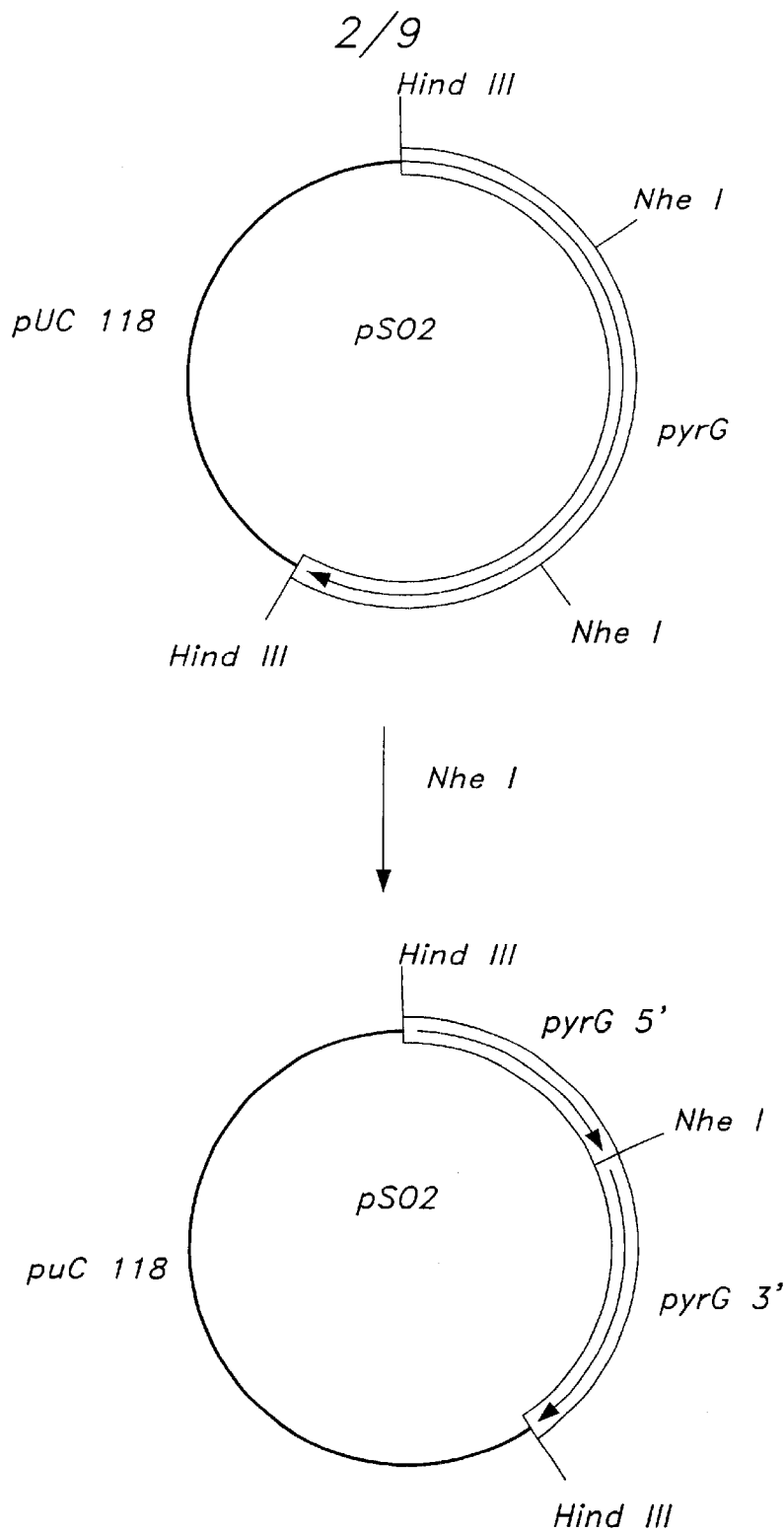
FIG. 2 diagrams the construction of the plasmid pSO5 which harbours 5' and 3' sequences from pyrG gene.

A pyrG deletion plasmid, pSO5, was constructed from the plasmid pSO2 by digestion with NheI to remove the gene encoding sequence of about 1.1 kb, then religated, leaving about 1 kb each of the pyrG 5' and 3' flanking sequences. The construction is illustrated in FIG. 2.

Construction of an *Aspergillus oryzae* pyrG⁻ Strain, HowB101

*A. oryzae* IFO 4177 was transformed with the 2.2 kb HindIII fragment from pSO5 harbouring the 5' and the 3' flanking sequence of the *A. oryzae* pyrG gene. The transformants were selected by resistance to 5-fluoro-orotic acid, a phenotype used to select for pyrG mutants. One transformant, HowB101, was shown by Southern analysis to contain the expected deletion at the pyrG locus. Because HowB101 is uridine dependent, it can be transformed with the wild type pyrG gene and transformants selected by the ability to grow in the absence of uridine.

Construction of an Alp Deletion Plasmid, pJaL212

A genomic DNA library from *A. oryzae* IFO 4177 was obtained by partial digestion with Sau3A. Fragments were ligated into BamHI-digested pUC19. The library was screened using degenerate oligonucleotide probes complementary to known protein sequence fragments of *A. oryzae* alkaline protease. A plasmid containing a 3.9 kb Sau3A fragment was obtained by this screening and named pSRe403.

pSRe403 was digested with SacII, then religated, to produce a plasmid in which a fragment of the alp gene about 1 kb in length had been deleted. The resultant plasmid was named pSRe403ΔSacII.

pSRe403ΔSacII was partially digested with HindIII, the ends were filled in using Klenow polymerase, then religated to remove the HindIII site in the pUC19 sequence, resulting in a plasmid which was named pJaL173.

Figure 3:
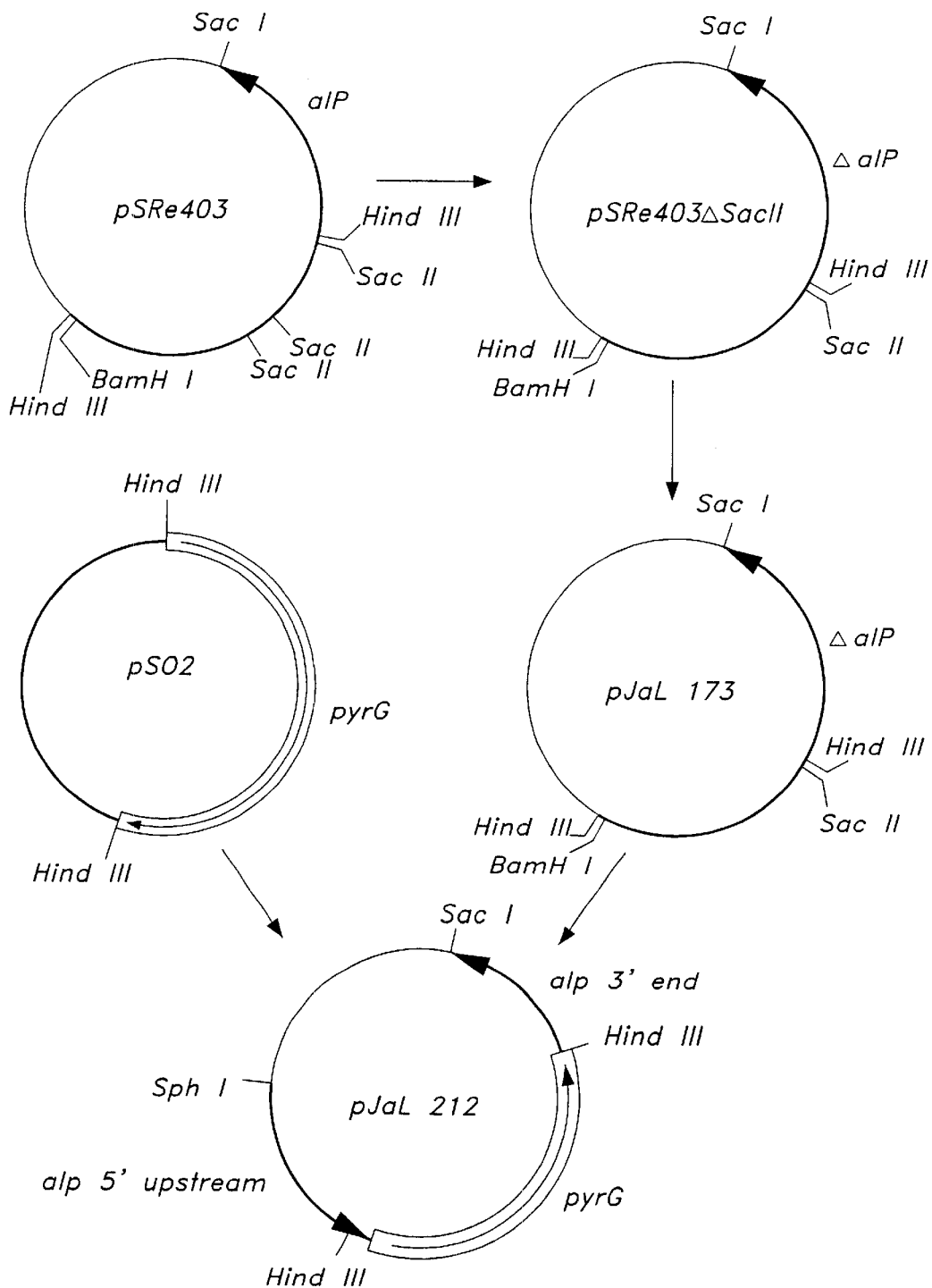
FIG. 3 diagrams the construction of the plasmid pJaL212 in which the pyrG coding sequence has been inserted between 5' and 3' sequences of the alp gene.

A 3.8 kb fragment containing the pyrG gene resulting from HindIII digestion of pSO2 was inserted into the HindIII site in pJa173 to produce a plasmid containing the HindIII fragment of the pyrG gene flanked by 5' and 3' sequences of the alp gene at the upstream and downstream positions, respectively. FIG. 3 summarizes the construction of plasmid, which was named pJaL212.

Construction of an *Aspergillus oryzae* alp⁻ Strain, JaL125

HowB101 was transformed with the 6.8 kb SacI/SphI fragment from pJaL212 using standard procedures. This fragment consists of 1.5 kb of the alp promoter, the pyrG gene and 1.5 kb of the 3' terminus of the alp gene. Transformants were selected by their ability to grow in the absence of uridine.

The transformants were analysed by Southern blotting in which a 599 bp PstI/SacII fragment from pJaL 173 harboring part of the alp gene served as a radioactively labelled probe. Strains carrying a deletion of the alp gene were recognised by a shift of the wild type PstI band from 1.0 kb to a 1.9 kb band. Four such transformants were identified, one of which was named JaL125.

Cloning of the *Aspergillus oryzae* NpI Gene

A cosmid library of *A. oryzae* was constructed using the SuperCos1 Cosmid Vector Kit following without modification the instructions provided by the supplier (Stratagene, Inc., La Jolla, Calif., USA).

Genomic DNA from *A. oryzae* IFO 4177 was prepared from protoplasts isolated by standard procedures (cf. e.g. Christensen, T., et. al., 1988. Biotechnology 6:1419–1422). After isolation, the protoplasts were pelleted by centrifugation at 2500 rpm for 5 minutes in a Labofuge T (Heto). The pellet was then suspended in a buffer of 10 mM NaCl, 20 mM Tris-HCl (pH 8.0), 1 mM EDTA, and treated with 100 μg/ml proteinase K and 0.5% SDS. This and all subsequent steps in the DNA preparation were performed following the recommended procedure of the SuperCos1 Cosmid Vector Kit.

The size of the genomic DNA was analysed by electrophoresis using the CHEF-gel apparatus from BioRad (Hercules, Calif., USA). Briefly, a 1% agarose gel was run for 20 hours at 200 volts with a 10–50 second pulse. The gel was stained with ethidium bromide and photographed under UV exposure, revealing DNA ranging from 50 to more than 100 kb in length. The DNA was then partially digested with Sau3A. The size of the resultant DNA fragments ranged from 20 to 50 kb as determined above by CHEF-gel analysis.

The CsCl gradient banded SuperCos1 vector was prepared, ligated and packaged according to the procedures provided with the kit. After titration of the library all of the packaging mix from a single ligation and packaging was transfected into the host cells XL1-Blue MR provided with the vector kit and plated onto LB plates containing 50 μg/ml ampicillin. Approximately 3800 colonies were obtained. Analysis of the cosmid preparation from 10 colonies indicated that all had inserts of the expected size. The colonies were individually picked and inoculated onto 96-well microtiter plates containing 100 μl LB and 100 μg/ml ampicillin per well, then incubated at 37° C. overnight. One hundred microliters of 50% glycerol was added to each well, and the entire library was frozen at −80° C. A total of 3822 colonies were stored, representing an approximate 4.4 fold amplification of the *A. oryzae* genome.

Preparation of a *Fusafium oxysporum* p45 Metalloprotease Probe

The *Fusarium oxysporum* p45 metalloprotease gene was cloned as disclosed in patent application WO 95/30757 (Novo Nordisk Biotech, Inc.), published Nov. 16, 1995.

A clone from the above cDNA library was selected and designated pDM115. A probe was prepared from pDM115 containing a 1.76 kb fragment of the *Fusarium oxysporum* cDNA that encodes a portion of the p45 gene. This plasmid was digested with SalI, and the fragments were separated on a 1% agarose gel. The band of interest was a 1.5 kb fragment from which the DNA was eluted. This fragment was labelled with $^{32}$P-dATP by random priming and used as a probe for Southern analysis and to screen an *A. oryzae* cosmid library.

Screening of the *A. oryzae* Library

To screen the *A. oryzae* cosmid library with the *Fusarium oxysporum* p45 probe, the individually frozen colonies in the library were inoculated onto LB plates containing 100 µg/ml ampicillin by using a multipin device in a configuration of 6 rows of 8 pins, designed to fit into half of a 96-well microtiter dish. Plates, containing colonies from all clones in the library, were incubated at 37° C. overnight. Sterilized Whatman 540 filters cut to fit the petri dishes were placed over the colonies which were then incubated for two more hours at 37° C. The filters were transferred to LB plates containing 200 µg/ml of chloramphenicol, and the plates were incubated overnight at 37° C. The next day the filters were washed twice in 0.5M NaOH for 5 minutes, then twice in 0.5M Tris-HCl (pH 7.4) for 5 minutes and finally twice in 2×SSC for 5 minutes. The filters were wet down with ethanol and allowed to air dry.

The filters were hybridised with the 1.5 kb $^{32}$P-labelled DNA fragment from pDM 115. The hybridisation was carried out for 16 hours at 65° C. in a standard hybridisation buffer of 10×Denhart's solution, 5×SSC, 0.02 M EDTA, 1% SDS, 0.15 mg/ml polyA RNA and 0.05 mg/ml yeast tRNA. After hybridisation the filters were washed in 2×SSC, 0.1% SDS at 65° C. twice and exposed to X-ray films. Three colonies showed hybridisation to the probe, 3E8, 3C1 and 2A5.

Characterisation of the Cosmid Clones

Restriction analysis revealed that two of the three cosmid clones, 3E8 and 3C1, contain inserts derived from the same region of the *A. oryzae* genome. Three micrograms of cosmid DNA was digested with EcoRi and fractionated by agarose gel electrophoresis. The DNA was transferred to Immobilan-N membrane filters (Millipore) and hybridised with the radio-labelled pDM115 probe. The results revealed that the probe hybridised to a 4 kb EcoRI fragment in both cosmid clones. The 4.0 kb EcoRI fragment was subjected to further analysis.

Construction of the NpI Deletion Plasmid, pJaL399

Plasmid pToC65, described in EP 531 372, was digested with Sacd, and treated with bacterial alkaline phosphatase according to the manufacturer's instructions (Boehringer Mannheim) to remove the 5' phosphate groups, then phenol extracted and precipitated. The 5.5 kb SacI fragment from cosmid clone 3E8 containing the *A. oryzae* NpI gene was isolated by gel electrophoresis and purified. The two fragments were mixed together and ligated. After tranformation into *E.coli*, the colonies carrying the correct plasmid were identified by restriction enzyme digestion of mini-plasmid preparations; the recovered plasmid was called pJaL389.

The presence of the coding region of the *A. oryzae* NpI gene was confirmed by DNA sequence analysis of portions of this subclone.

Figure 4:
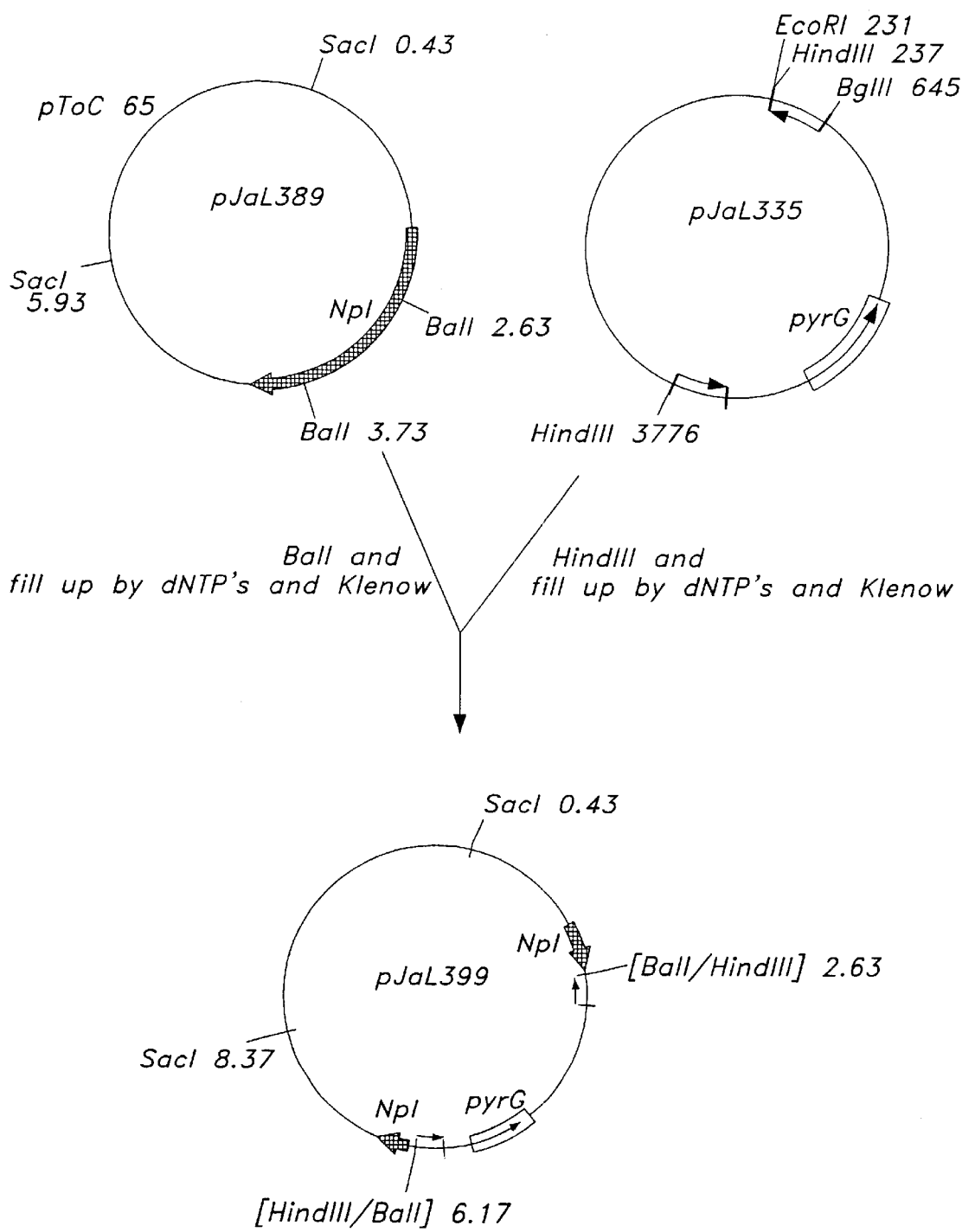
FIG. 4 diagrams the construction of the plasmid pJaL399 in which the NpI encoding sequence is disrupted.

Plasmid pJaL389 was digested with BalI to delete an internal 1.1 kb fragment of the NpI gene. The remaining 7.1 kb fragment was treated with Klenow polymerase to create blunt ends, then isolated by gel electrophoresis and purified. This DNA fragment was next treated with bacterial alkaline phosphatase, phenol extracted and precipitated. Plasmid pJaL335 was digested with HindIII to obtain a 3.5 kb fragment comprising the *A. oryzae* pyrG gene, then similarly treated with Klenow polymerase, isolated by gel electrophoresis, and purified. The two fragments were mixed together and ligated. After transformation into *E.coli*, the colonies carrying the correct plasmid were identified by restriction enzyme digestion of mini-plasmid preparations. The construction of this plasmid, called pJaL399, is summarised in FIG. 4.

Thus, plasmid pJaL399 contains a fragment of the pToC65 vector harbouring the NpI ogene in which the internal 1.1 kb BalI fragment has been replaced with a 3.5 kb DNA fragment encoding the *A. oryzae* pyrG gene.

Isolation of a pyrG⁻ *A. oryzae* Strain, JaL151

The *A. oryzae* alp⁻ strain, JaL125, was screened for resistance to 5-flouro-orotic acid to identify spontaneous pyrG mutants. One strain, named JaL151, was identified as being alp⁻ and pyrGu⁻. As with HowB101, JaL151 is uridine dependent, therefore it can be transformed with the wild type pyrG gene and transformants selected by the ability to grow in the absence of uridine.

Construction of an Aspergillus oryzae NpI⁻ Strain, JaL228

JaL151 was transformed with the 7.9 kb SaI fragment of pJaL399 using standard procedures. Transformants were then selected by their ability to grow in the absence of uridine. After reisolation chromosomal DNA was prepared from 12 transformants. The DNA from each of the transformants was digested with BalI and analysed by Southern blotting, using the 5.5 kb $^{32}$P-labelled DNA SaI fragment from pJaL389 containing the NpI gene as described above as the probe. Strains of interest were identified by the absence of the 1.1 kb BalI hybridising fragment, indicating a disruption of the NpI gene, as well as by showing an altered mobility of the flanking 5' and 3' sequences. The strain resulting from one of these transformants was named JaL228.

Example 2

Cloning of *C. antarctica* Lipase B

Figure 5:
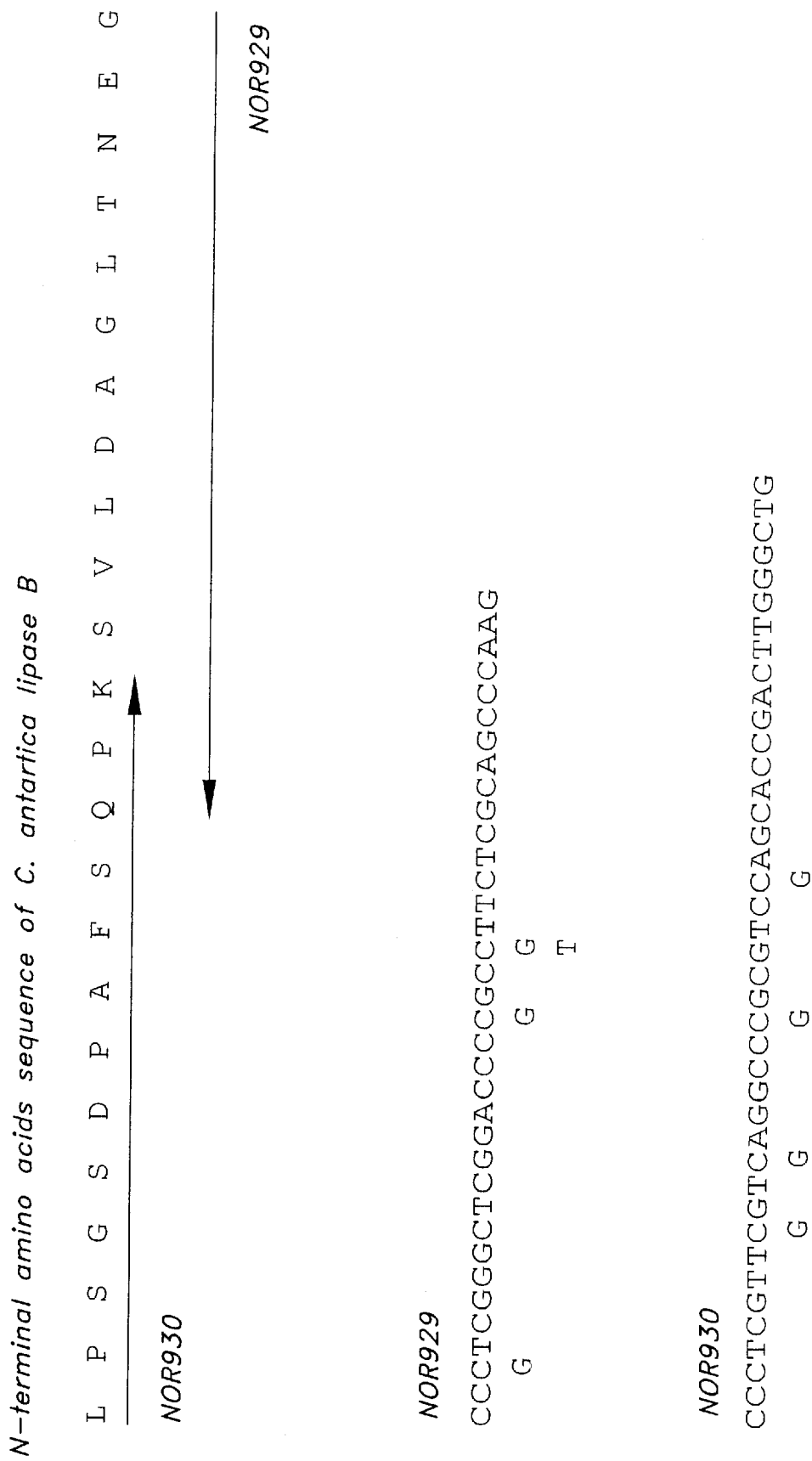
FIG. 5 shows the N-terminal amino acid sequence of *Candida antarctica* lipase B and the sequences of two oligonucleotide primers derived from this sequence (SEQ ID NOS: 4 and 5)
Figure 6:
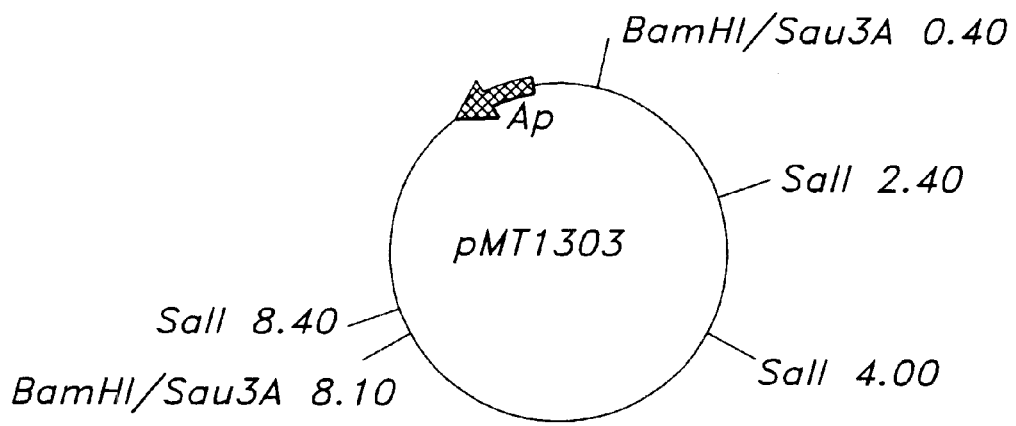
FIG. 6 diagrams the construction of plasmid pMT1305 which harbours the *C. antarctica* lipase B gene.
Figure 6:
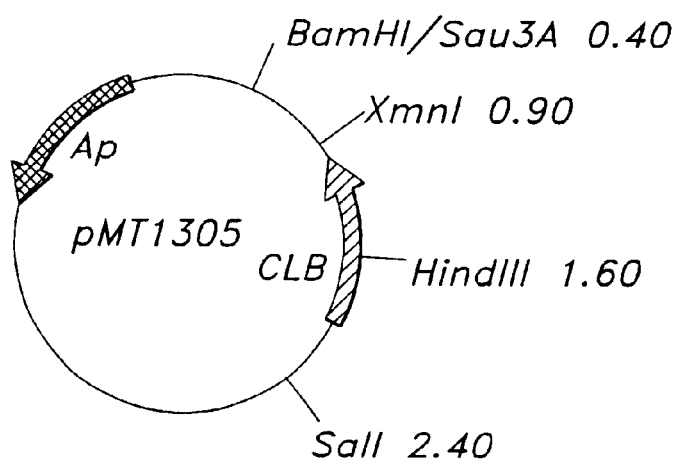

A partial Sau3A digested *Candida antarctica* genomic library in pBR322 was prepared and replica filters were screened with two oligonucleotide probes designed from the N-terminal amino acid sequence of clb, NOR929 (SEQ. ID. No. 4) and NOR930 (SEQ. ID. No. 5) (FIG. 5). Eight colonies were identified. Analysis of the plasmids indicated overlapping inserts. One of the plasmids, pMT1303, containing a 7.8 bp insert, was further analysed. By deleting the SalI fragment a plasmid, pMT1305, containing a 2.1 kb insert was constructed (FIG. 6). Using NOR929 as a template, pMT1305 was sequenced to confirm that clb (*C. antarctica* lipase B) was encoded. The entire gene was sequenced in both strands by making a series of deletions in pMT1305 using the Promega Erase-a-Base© system (Promega Corp., Madison Wis., USA). The coding sequence is given in SEQ. ID. No. 6.

Construction of a Partial CLB Plasmid, pMT1329

Figure 7:
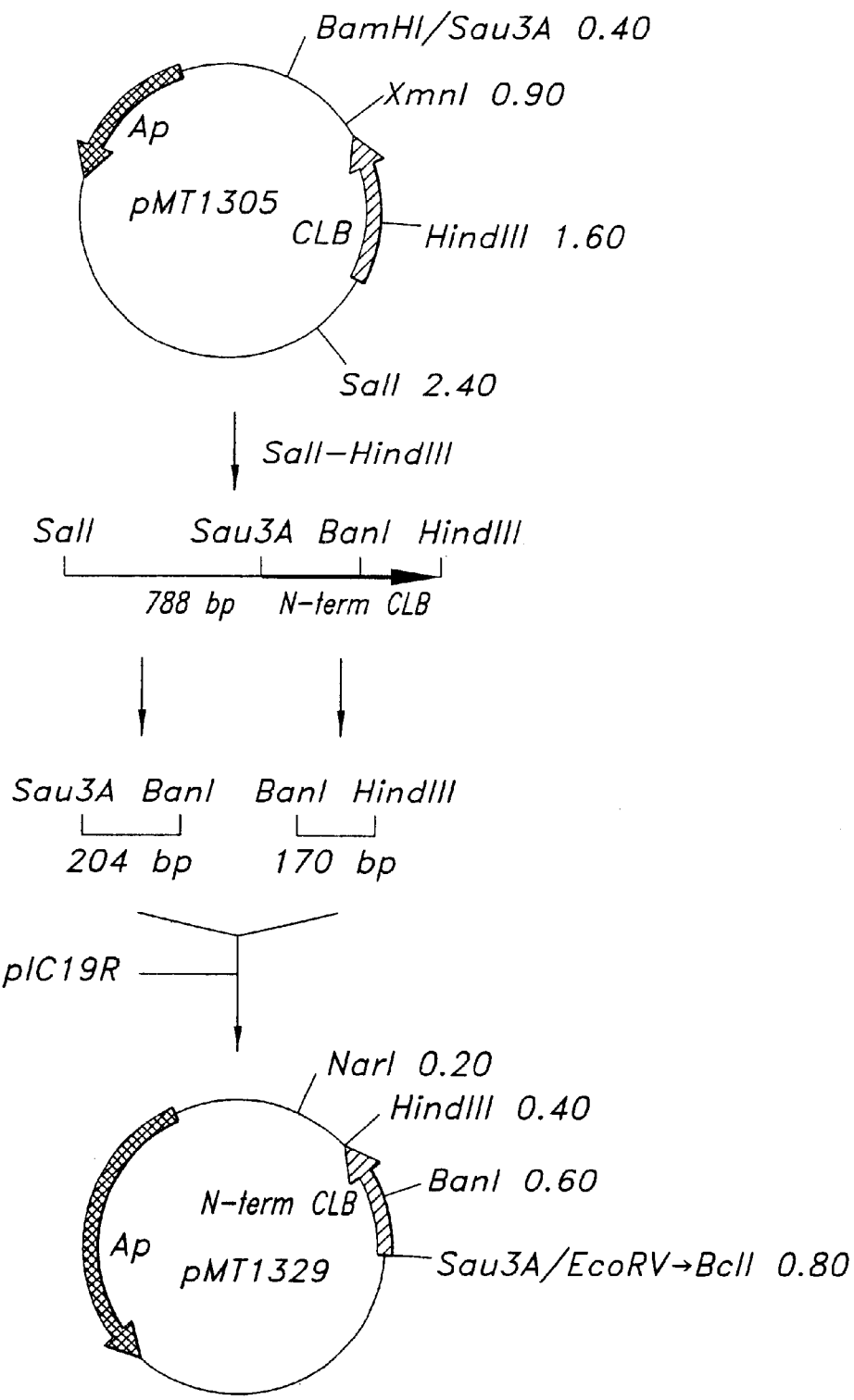
FIG. 7 diagrams the construction of the plasmid pMT1329 which harbours partial sequence from the 5' end of the *C. antarctica* lipase B gene.

A 788 bp SalI-HindIII fragment encoding the N-terminal sequence for CLB was isolated from pMT1305. From this fragment two smaller fragments were isolated, a 170 bp HindIII-BanI and a 204 bp BanI filled-in Sau3A. These two fragments were cloned into the plasmid pIC19R, which had been digested with EcoRV and HindIII. This created a BclI site at the EcoRV and filled-in Sau3A site 9 bp adjacent to the ATG codon for clb, resulting in the plasmid named pMT1329 (FIG. 7).

Construction of a Partial CLB Plasmid, pMT1332

Figure 8:
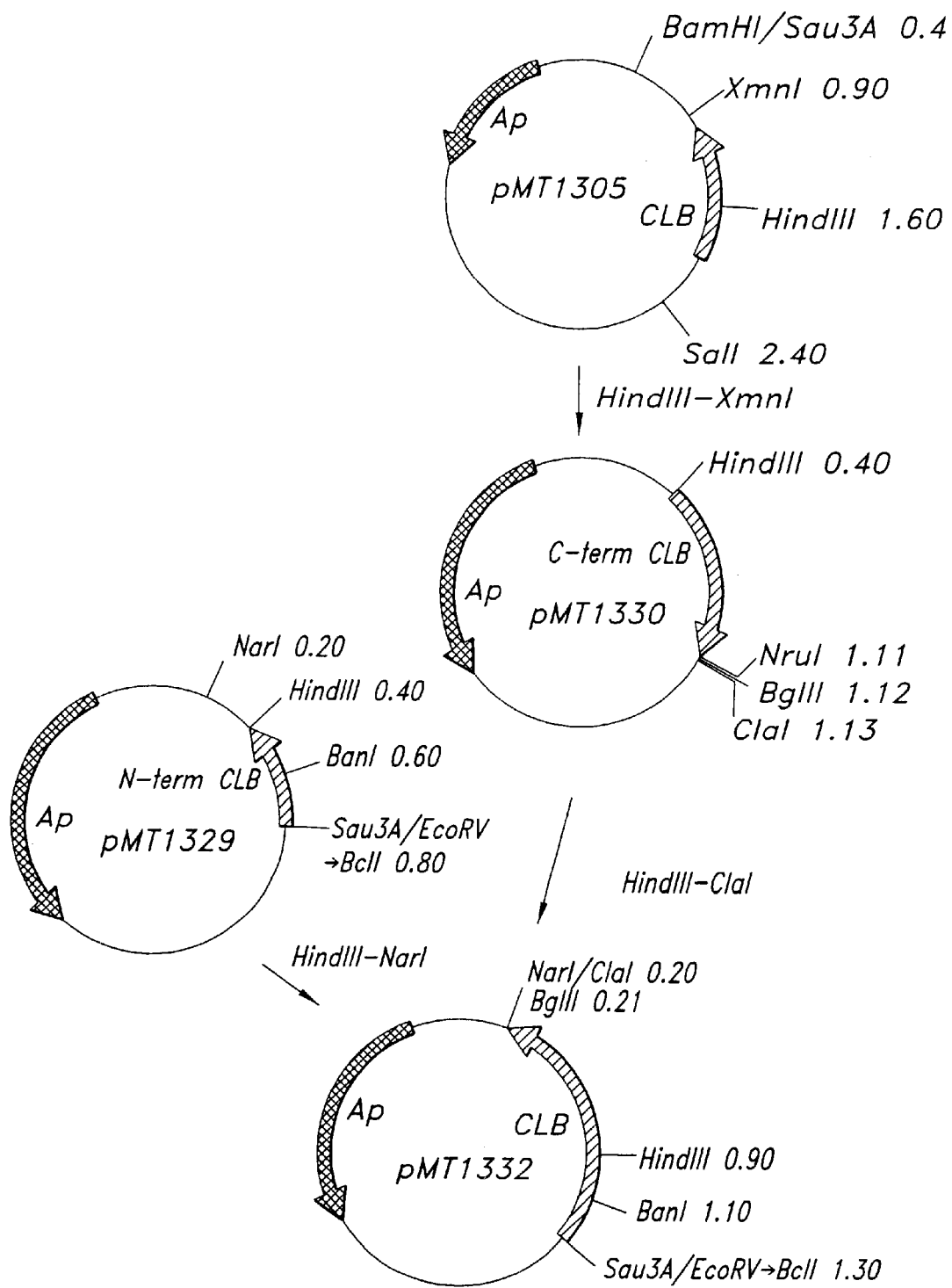
FIG. 8 diagrams the construction of the plasmid pMT1332 which harbours the *C. antarctica* lipase B gene.

The gene sequence encoding the C-terminal region of CLB was isolated as a 670 bp HindIII-Xmn1 fragment from pMT1305 and inserted into plasmid pIC7, which had been digested with HindIII-NruI , resulting in pMT1330. The complete gene was assembled from the 3.0 kb HindIII-NarI fragment from pMT1329 and the 0.7 kb HindIII-Cla1 fragment from pMT1330, resulting in pMT1332 (FIG. 8).

Construction of a CLB Expression Plasmid, pMT1335

Figure 9:
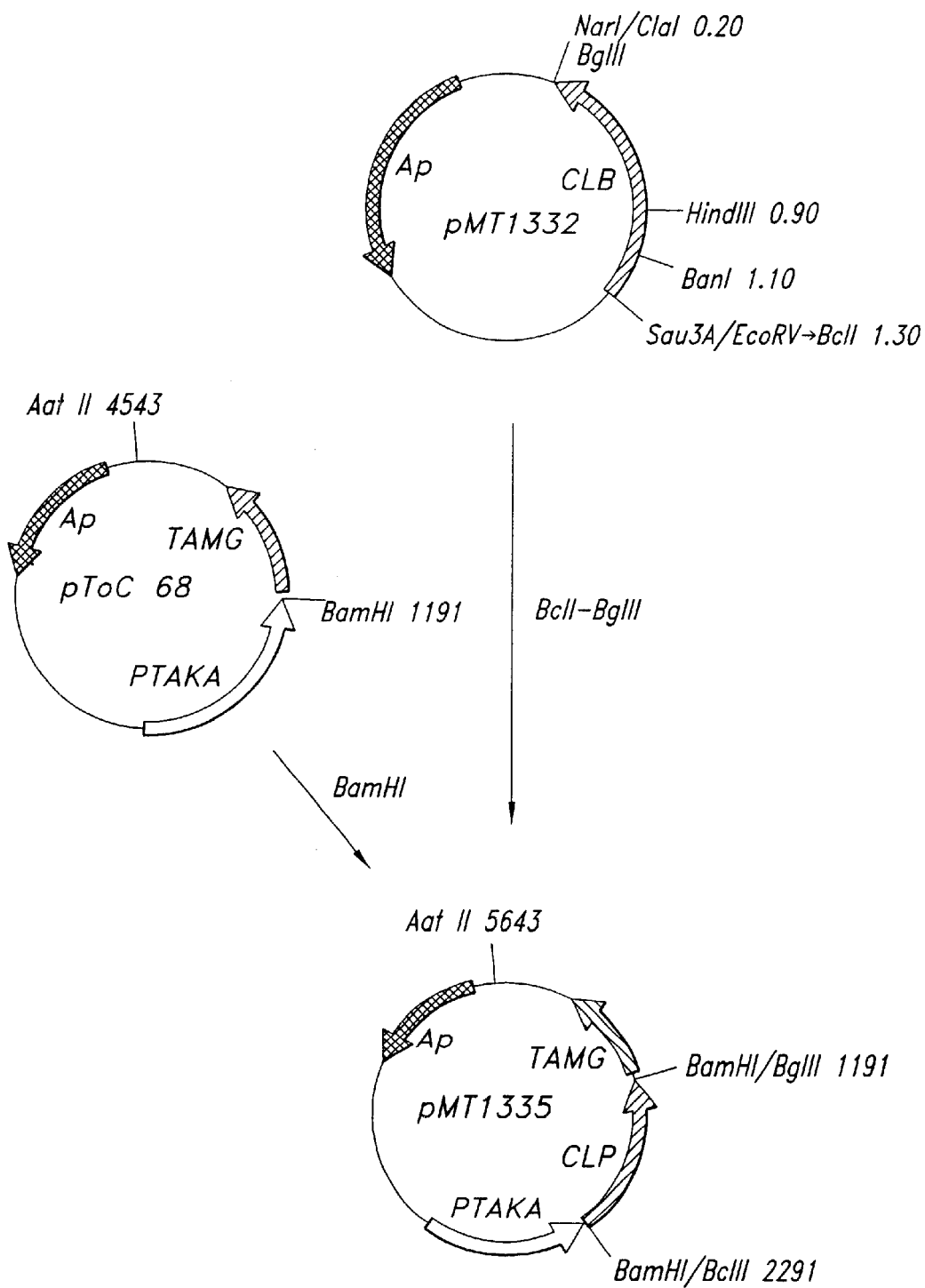
FIG. 9 diagrams the construction of the expression plasmid pMT1335 which harbours the *C. antarctica* lipase B gene.

The clb gene was expressed in Aspergillus using the expression vector pToC68. The 1 kb BclI-BglII fragment from pMT1332 was inserted into pToC68, which had been digested with BamHI, to give pMT1335 (FIG. 9). Thus, the construction of the plasmid pMT1335 resulted in a fungal expression plasmid for the *C. antarctica* lipase B gene.

Expression of *C. antartica* Lipase B in *Aspergillus oryzae* Strains

*A. oryzae* strains IFO 4177 and JaL228 were transformed with pMT1335 by co-transformation with pToC90 (need to define pToC90).

Transformants were selected for growth on minimal medium containing 10 mM acetamide and screened for the presence of pMT1335 by the ability to produce CLB. One transformant from each of the *A. oryzae* wild type strain IFO 4177 and the alp⁻, NpI⁻ strain JaL228 was selected for tank fermentation run for 93 hours. Conidiospores were inoculated into 2-liter Keiler fermentors at 30° C. containing 1.2 liter 20% maltose liquor and 8% urea. A mixture of 20% maltose liquor and 8% urea was added continuously; phosphoric acid was added as necessary to maintain a pH of 7.

Summarised in Table 1 below is the yield of CLB activity from JaL228 in comparison to IFO4177, in which one lipase unit (LU) is defined as the amount of enzyme needed to liberate 1 $\mu$mol of butyric acid per minute from tributyrin at pH 7.0 and at 30° C. The table indicates that the amount produced in JaL228 is 1.8 times greater than in IFO 4177, demonstrating that the deletion of the alp and NpI genes can significantly improve the stability of proteins sensitive to the activity of these proteases.

TABLE 1

CLB production by IFO 4177 and JaL228 after tank fermentation for 93 hours.

| Hours | IFO4177 LU/g | JaL228 LU/g |
|---|---|---|
| 93 | 575 | 1041 |

What is claimed is:

1. A method of producing a protein, comprising:
   (a) cultivating a filamentous fungal cell in a suitable growth medium wherein the cell comprises (i) a DNA sequence encoding the protein wherein the protein is a heterologous protein, and (ii) a DNA sequence encoding a metalloprotease and a DNA sequence encoding an alkaline protease, which are partially or completely inactivated, wherein the DNA sequence encoding the metalloprotease is at least 70% identical with SEQ ID NO:1 and/or SEQ ID NO 2 and the DNA sequence encoding the alkaline protease is at least 70% identical with SEQ ID NO 3; and
   (b) recovering the protein.

2. The method of claim 1, wherein the DNA sequence encoding the metalloprotease is at least 80% identical with SEQ ID NO:1 or SEQ ID NO 2.

3. The method of claim 2, wherein the DNA sequence encoding the metalloprotease is at least 90% identical with SEQ ID NO:1 or SEQ ID NO 2.

4. The method of claim 3, wherein the DNA sequence encoding the metalloprotease is at least 95% identical with SEQ ID NO:1 or SEQ ID NO 2.

5. The method of claim 4, wherein the DNA sequence encoding the metalloprotease is at least 97% identical with SEQ ID NO:1 or SEQ ID NO 2.

6. The method of claim 5, wherein the DNA sequence encoding the metalloprotease is SEQ ID NO:1 or SEQ ID NO 2.

7. The method of claim 1, wherein the DNA sequence encoding the alkaline protease is at least 80% identical with SEQ ID NO:3.

8. The method of claim 7, wherein the DNA sequence encoding the alkaline protease is at least 90% identical with SEQ ID NO:3.

9. The method of claim 8, wherein the DNA sequence encoding the alkaline protease is at least 95% identical with SEQ ID NO:3.

10. The method of claim 9, wherein the DNA sequence encoding the alkaline protease is at least 97% identical with SEQ ID NO:3.

11. The method of claim 10, wherein the DNA sequence encoding the alkaline protease is SEQ ID NO 3.

12. The method of claim 1, wherein the DNA sequence encoding the metalloprotease is SEQ ID NO:1 or SEQ ID NO 2 and the DNA sequence encoding the alkaline protease is SEQ ID NO 3.

13. The method of claim 1, wherein the cell is an Acremonium, Aspergillus, Candida, Cochliobolus, Endothia, Fusarium, Humicola, Neurospora, Podospora, Penicillium, Pyricularia, Rhizomucor, Rhizopus, Thermomyces, or Trichoderma strain.

14. The method of claim 13, wherein the cell is an *Aspergillus awamori, Aspergillus foetus, Aspergillus japonicus, Aspergillus nidulans, Aspergillus niger, Aspergillus oryzae, Aspergillus phoenicis*, Fusarium ATCC 20334, *Fusarium oxysporum, Fusarium solani, Humicola grisea, Neurospora cressa, Penicillium chrysogenum, Rhizomucor miehel, Trichoderma reesei*, and *Trichoderma viride* cell.

15. The method of claim 14, wherein the cell is an *Aspergillus oryzae* cell.

16. The method of claim 1, wherein the protein is a therapeutically active protein.

17. The method of claim 1, wherein the protein is a fungal protein.

18. The method of claim 17, wherein the fungal protein is an amylolytic enzyme, cellulytic enzyme, cutinase, laccase, lipolytic enzyme, oxidoreductase, pectinase, proteolytic enzyme, or xylanolytic enzyme.

19. The method of claim 1, wherein the protein is a bacterial protein.

20. The method of claim 1, wherein the protein is a precursor protein.

* * * * *